(12) United States Patent
Fagan et al.

(10) Patent No.: US 12,161,355 B2
(45) Date of Patent: Dec. 10, 2024

(54) ARTICULATING ULTRASONIC SURGICAL INSTRUMENTS AND SYSTEMS

(71) Applicant: Covidien LP, Mansfield, MA (US)

(72) Inventors: James R. Fagan, Erie, CO (US); Thomas E. Drochner, Longmont, CO (US); Matthew S. Cowley, Fredrick, CO (US); Michael B. Lyons, Boulder, CO (US)

(73) Assignee: Covidien LP, Mansfield, MA (US)

( * ) Notice: Subject to any disclaimer, the term of this patent is extended or adjusted under 35 U.S.C. 154(b) by 809 days.

(21) Appl. No.: 17/320,360

(22) Filed: May 14, 2021

(65) Prior Publication Data

US 2021/0353325 A1 Nov. 18, 2021

Related U.S. Application Data

(60) Provisional application No. 63/026,377, filed on May 18, 2020, provisional application No. 63/026,323, filed on May 18, 2020.

(51) Int. Cl.
*A61B 17/32* (2006.01)
*A61B 8/00* (2006.01)

(52) U.S. Cl.
CPC .... *A61B 17/320068* (2013.01); *A61B 8/4427* (2013.01); *A61B 8/445* (2013.01); *A61B 17/320016* (2013.01)

(58) Field of Classification Search
CPC ....... A61B 17/32; A61B 17/068; A61B 17/32; A61B 17/320092; A61B 17/320068; A61B 2017/320072; A61B 8/445; A61B 8/4427
See application file for complete search history.

(56) References Cited

U.S. PATENT DOCUMENTS

| | | |
|---|---|---|
| 5,897,523 A | 4/1999 | Wright et al. |
| 6,051,010 A | 4/2000 | DiMatteo et al. |
| 6,063,098 A | 5/2000 | Houser et al. |
| 6,589,200 B1 | 7/2003 | Schwemberger et al. |
| 6,752,815 B2 | 6/2004 | Beaupre |

(Continued)

FOREIGN PATENT DOCUMENTS

WO 2019018289 A1 1/2019

OTHER PUBLICATIONS

Partial European Search Report dated Sep. 30, 2021 issued in corresponding EP Appln. No. 21174201.0.

(Continued)

*Primary Examiner* — Vi X Nguyen

(57) ABSTRACT

A surgical instrument includes a housing having an elongated body extending distally therefrom. The elongated body defines a first articulating portion and a second articulating portion. The elongated body defines a lumen therein. An end effector is supported at a distal end portion of the elongated body. A flexible waveguide extends through the lumen of the elongated body. A proximal end portion of the flexible waveguide connects to an ultrasonic transducer. A distal end portion of the flexible waveguide is connected with the end effector. the flexible waveguide defines a first articulating portion having a narrower thickness than a thickness of other portions of the flexible waveguide and a second articulating portion having a narrower thickness than a thickness of other portions of the flexible waveguide.

16 Claims, 28 Drawing Sheets

(56) References Cited

U.S. PATENT DOCUMENTS

| | | |
|---|---|---|
| 6,783,524 B2 | 8/2004 | Anderson et al. |
| 7,135,030 B2 | 11/2006 | Schwemberger et al. |
| 7,837,699 B2 | 11/2010 | Yamada et al. |
| 7,922,651 B2 | 4/2011 | Yamada et al. |
| 9,095,367 B2 | 8/2015 | Olson et al. |
| 9,314,308 B2 | 4/2016 | Parihar et al. |
| 9,393,037 B2 | 7/2016 | Olson et al. |
| 9,408,622 B2 | 8/2016 | Stulen |
| 9,655,614 B2 | 5/2017 | Swensgard et al. |
| 10,029,125 B2 | 7/2018 | Shapiro et al. |
| 10,034,683 B2 | 7/2018 | Monroe et al. |
| 10,172,636 B2 | 1/2019 | Stulen et al. |
| 10,226,274 B2 | 3/2019 | Worrell et al. |
| 10,258,363 B2 | 4/2019 | Worrell et al. |
| 10,413,316 B2 | 9/2019 | Lyons |
| 2006/0058825 A1 | 3/2006 | Ogura et al. |
| 2014/0005701 A1 | 1/2014 | Olson et al. |
| 2014/0005702 A1 | 1/2014 | Timm et al. |
| 2014/0276931 A1 | 9/2014 | Parihar et al. |
| 2014/0309562 A1 | 10/2014 | Ito |
| 2014/0350570 A1 | 11/2014 | Lee |
| 2015/0080924 A1 | 3/2015 | Stulen et al. |
| 2015/0157355 A1 | 6/2015 | Price et al. |
| 2015/0320437 A1* | 11/2015 | Worrell .......... A61B 17/320068 606/169 |
| 2015/0320438 A1 | 11/2015 | Weisenburgh, II et al. |
| 2016/0302812 A1 | 10/2016 | Monroe et al. |
| 2016/0302818 A1 | 10/2016 | Weisenburgh, II et al. |
| 2016/0302819 A1 | 10/2016 | Stulen et al. |
| 2017/0135718 A1 | 5/2017 | Lyons |
| 2017/0202595 A1* | 7/2017 | Shelton, IV ....... A61B 18/1445 |
| 2017/0245875 A1 | 8/2017 | Timm et al. |
| 2017/0281218 A1 | 10/2017 | Timm |
| 2017/0281220 A1 | 10/2017 | Hibner et al. |
| 2018/0168681 A1 | 6/2018 | Kirk et al. |
| 2019/0021752 A1 | 1/2019 | Boudreaux |
| 2019/0021756 A1 | 1/2019 | Boudreaux |
| 2019/0029712 A1 | 1/2019 | Stoddard et al. |
| 2019/0133635 A1 | 5/2019 | Stulen et al. |

OTHER PUBLICATIONS

Extended European Search Report dated Jan. 5, 2022 issued in corresponding EP Appln. No. 21174201.0.

\* cited by examiner

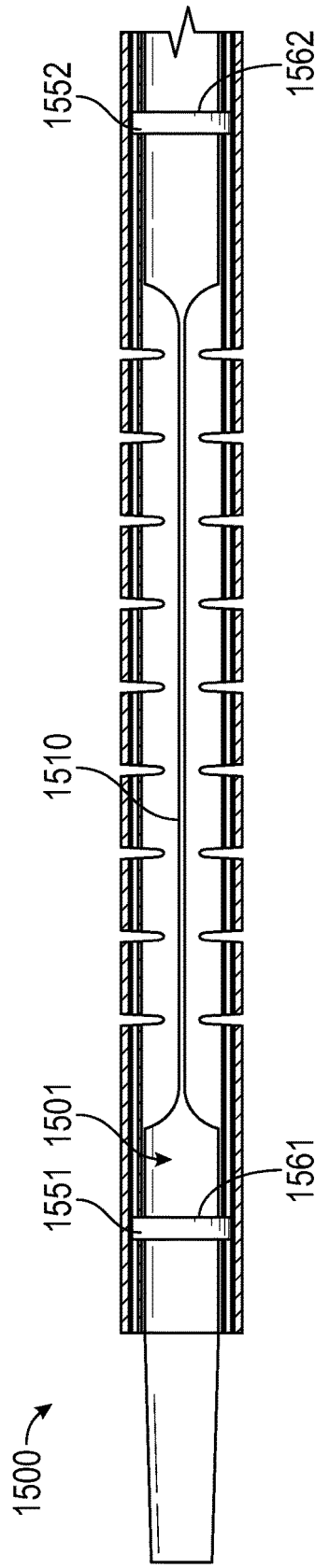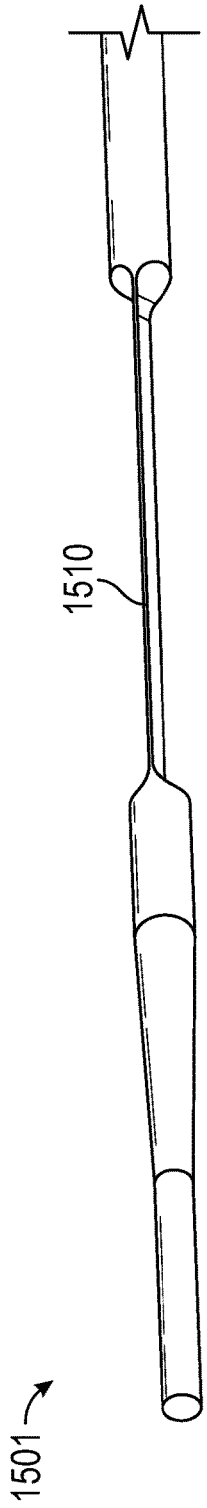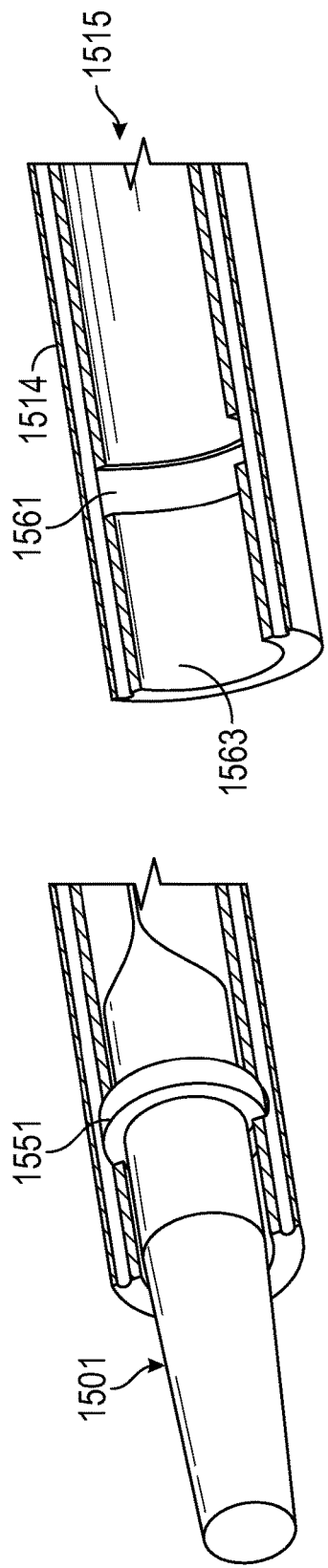
FIG. 15A
FIG. 15B
FIG. 15C
FIG. 15D

ARTICULATING ULTRASONIC SURGICAL INSTRUMENTS AND SYSTEMS

CROSS-REFERENCE TO RELATED APPLICATIONS

The present application claims the benefit of and priority to U.S. Provisional Patent Applications Nos. 63/026,377 and 63/026,323, each of which was filed on May 18, 2020. The entire contents of each of the foregoing applications are incorporated by reference herein.

FIELD

The present disclosure relates to surgical instruments and systems and, more particularly, to articulating ultrasonic surgical instruments and systems.

BACKGROUND

Ultrasonic surgical instruments and systems utilize ultrasonic energy, i.e., ultrasonic vibrations, to treat tissue. More specifically, a typical ultrasonic surgical instrument or system includes a transducer configured to produce and transmit mechanical vibration energy at ultrasonic frequencies along a waveguide to an ultrasonic end effector configured to treat tissue, e.g., coagulate, cauterize, fuse, seal, cut, desiccate, or otherwise treat tissue. Traditionally, the transducer remains external of the surgical site, while the waveguide extends from the transducer into the surgical site to provide the ultrasonic energy to the ultrasonic end effector. The ultrasonic end effector is manipulated into position to treat a desired tissue or tissues.

Some ultrasonic surgical instruments and systems incorporate rotation features, thus enabling rotation of the ultrasonic end effector to a desired orientation within the surgical site. However, even in such instruments and systems, the ability to navigate within the surgical site via rotation and manipulation alone is limited.

SUMMARY

In one aspect of the disclosure, a surgical instrument includes a housing having an elongated body extending distally therefrom. The elongated body defines a first articulating portion and a second articulating portion. The elongated body defines a lumen therein. An end effector is supported at a distal end portion of the elongated body. A flexible waveguide extends through the lumen of the elongated body. A proximal end portion of the flexible waveguide connects to an ultrasonic transducer. A distal end portion of the flexible waveguide is connected with the end effector. The flexible waveguide defines a first articulating portion having a narrower thickness than a thickness of other portions of the flexible waveguide and a second articulating portion having a narrower thickness than a thickness of other portions of the flexible waveguide.

In some aspects of the disclosure, the first articulating portion of the flexible waveguide is configured to articulate in a first orientation, and the second articulating portion of the flexible waveguide is configured to articulate in a second orientation. The first articulating portion of the flexible waveguide and the second articulating portion of the flexible waveguide may each articulate in a same orientation as each other, or different orientations from each other. The first or second articulating portions of the flexible waveguide is configured to articulate from about 1 degree to about 45 degrees.

In some aspects of the disclosure, the end effector includes an ultrasonic blade and a jaw configured to rotate about the ultrasonic blade. The ultrasonic blade and the jaw are configured to capture and treat tissue therebetween in plural rotational orientations of the jaw relative to the ultrasonic blade.

In some aspects of the disclosure, the elongated body is configured to rotate to achieve different directional orientations of the end effector. Independent controls are configured to rotate the elongated body, rotate the jaw about the ultrasonic blade, and articulate the first articulating portion and the second articulating portion of the elongated body. Thus, the first articulating portion of the flexible waveguide and the second articulating portion of the flexible waveguide are correspondingly rotated by the independent controls.

In some aspects of the disclosure, first and second transducers are at opposite sides of the first articulating portion of the flexible waveguide. At least one of the first or second transducers is configured to amplify an ultrasonic wave transmitted through the first articulating portion of the flexible waveguide.

In some aspects of the disclosure, the flexible waveguide may define a single articulating portion having a narrower width than a width of other portions of the flexible waveguide, and the elongated body may be configured to rotate to achieve different directional orientations of the end effector.

In one aspect of the disclosure, an elongated body of a surgical instrument includes an inner tube including an articulating section and defining a lumen therethrough. An outer tube is disposed about the inner tube and includes a proximal portion and a distal portion. The proximal portion of the outer tube defines an articulating section. The articulating section of the outer tube at least partially overlaps the articulating section of the inner tube. The distal portion of the outer tube is slidable with respect to the proximal portion of the outer tube. An end effector assembly is disposed at a distal end portion of the inner tube. The end effector assembly includes an ultrasonic blade and a jaw configured to rotate about the ultrasonic blade. The jaw is configured to move between an open position and a clamping position with respect to the ultrasonic blade to capture and treat tissue therebetween in plural rotational orientations of the jaw relative to the ultrasonic blade. A flexible waveguide extends through the lumen of the inner tube. A distal end portion of the flexible waveguide is connected with the ultrasonic blade of the end effector assembly. Sliding the distal portion of the outer tube with respect to the proximal portion of the outer tube actuates the jaw with respect to the ultrasonic blade between the open position and the clamping position.

In some aspects of the disclosure, a cable extends along the proximal portion of the outer tube. The cable is operably coupled to the distal portion of the outer tube. The cable is configured to slide the distal portion of the outer tube in a proximal direction toward the proximal portion of the outer tube to actuate the jaw with respect to the ultrasonic blade to the clamping position. A spring is operably coupled to the distal portion of the outer tube. The spring is configured to bias the distal portion of the outer tube in a distal direction away from the proximal portion of the outer tube to bias the jaw with respect to the ultrasonic blade to the open position or a closed position.

In some aspects of the disclosure, a yoke is operably coupled to the cable and the distal portion of the outer tube.

Pulling the cable in the proximal direction pulls the distal portion of the outer tube in the proximal direction to actuate the jaw. The yoke is configured to allow the distal portion of the outer tube to rotate with respect to the proximal portion of the outer tube.

In some aspects of the disclosure, the yoke includes a first curved arm and a second curved arm. The first and second curved arms are configured to rotatably slide along a groove formed in the distal portion of the outer tube. The yoke includes a guide block extending along a longitudinal axis of the proximal portion of the outer tube. The guide block is configured to slide along the proximal portion of the outer tube.

In some aspects of the disclosure, a drive gear is operably coupled to the jaw assembly. An input gear is engaged with the drive gear. Rotation of the input gear rotates the drive gear to rotate the jaw assembly. A torque cable is operably coupled to the input gear. Rotation of the torque cable rotates the input gear.

In some aspects of the disclosure, the inner tube is rotatably coupled to the proximal portion of the outer tube.

In some aspects of the disclosure, the inner tube includes a groove and the proximal portion of the outer tube includes a retaining ring positioned in the groove to rotatably couple the inner tube to the proximal portion of the outer tube.

In some aspects of the disclosure, the distal portion of the outer tube includes at least one slot, and the inner tube includes at least one boss slidably positioned in the at least one slot. The at least one slot allows the distal portion of the outer tube to move proximally and distally with respect to the inner tube. The inner tube rotates in unison with the outer tube.

In some aspects of the disclosure, the outer tube includes at least one spiral cutout configured to allow articulation in any direction and apply a rotational force to the jaw. The inner tube includes a plurality of cutouts spaced apart from each other. The plurality of cutouts are configured to allow articulation of the inner tube substantially along a single plane.

In some aspects of the disclosure, a direct drive including at least two links extends along the outer tube. The direct drive is configured to drive opening and closing of the jaw.

Other features of the disclosure will be appreciated from the following description.

BRIEF DESCRIPTION OF THE DRAWINGS

The accompanying drawings, which are incorporated in and constitute a part of this specification, illustrate aspects and features of the disclosure and, together with the detailed description below, serve to further explain the disclosure, in which:

FIG. 15A is a longitudinal, cross-sectional view of a flexible waveguide secured within a lumen of an elongated body by a removable annular collar;

FIG. 15B is a perspective view of the flexible waveguide of FIG. 15A with the removable annular collar omitted;

FIG. 15C is a longitudinal, cross-sectional view of the removable annular collar positioned about the flexible waveguide and secured in the lumen by a recess formed in an inner surface of the elongated body of FIG. 15A;

FIG. 15D is a longitudinal, cross-sectional view of the recess of FIG. 15C;

DETAILED DESCRIPTION

Figure 1:
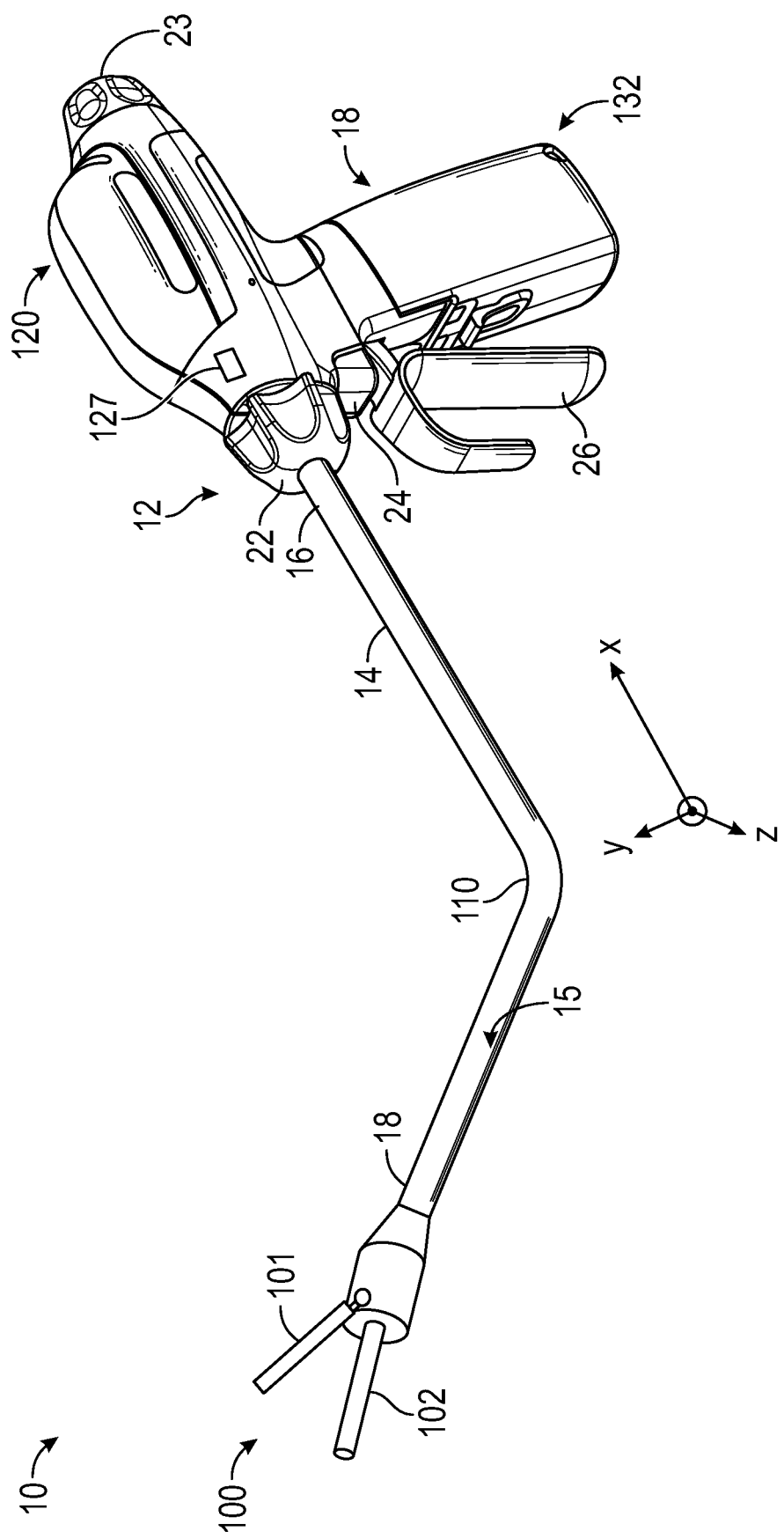
FIG. 1 is a side, perspective view of a surgical instrument having an articulating portion configured for use in accordance with the aspects and features of present disclosure.
Figure 2:
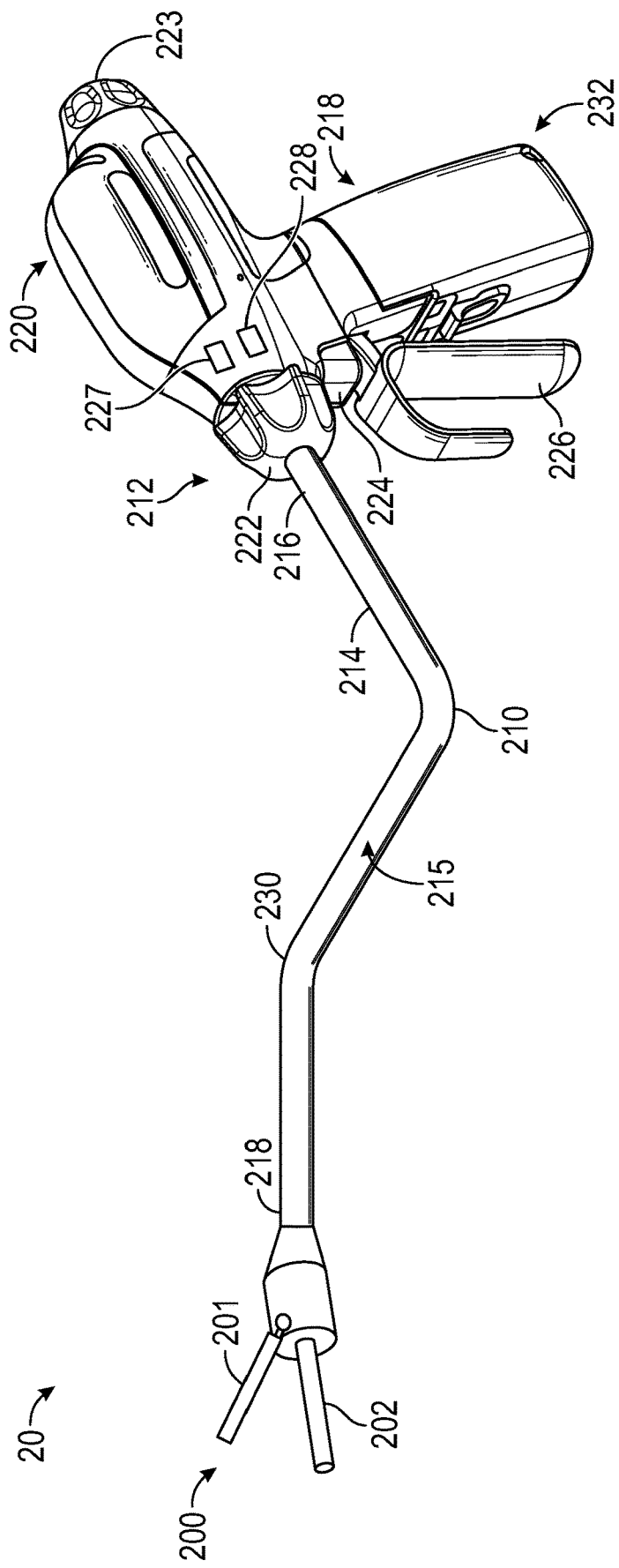
FIG. 2 is a side, perspective view of a surgical instrument having first and second articulating portions configured for use in accordance with the aspects and features of present disclosure.

As used herein, the term "distal" refers to the portion that is being described which is further from a user, while the term "proximal" refers to the portion that is being described which is closer to a user. Further, to the extent consistent, any of the aspects and features detailed herein may be used in conjunction with any or all of the other aspects and features detailed herein.

As used herein, the terms parallel and perpendicular are understood to include relative configurations that are substantially parallel and substantially perpendicular up to about + or −10 degrees from true parallel and true perpendicular.

Exemplary axes or directions such as an X-axis direction, a Y-axis direction and a Z-axis direction may be illustrated in the accompanying drawings and/or described herein. As an example, the X-axis direction may perpendicular to the Y-axis direction, and the Z-axis direction may be orthogonal to the X-axis direction and the Y-axis direction.

"About" or "approximately" or "substantially" as used herein may be inclusive of the stated value and means within an acceptable range of variation for the particular value as determined by one of ordinary skill in the art, considering the measurement in question and the error associated with measurement of the particular quantity (e.g., the limitations of the measurement system). For example, "about" may mean within one or more standard variations, or within ±30%, 20%, 10%, 5% of the stated value.

Descriptions of technical features or aspects of an exemplary embodiment of the disclosure should typically be considered as available and applicable to other similar features or aspects in another exemplary embodiment of the disclosure. Accordingly, technical features described herein according to one exemplary embodiment of the disclosure may be applicable to other exemplary embodiments of the disclosure, and thus duplicative descriptions may be omitted herein.

Exemplary embodiments of the disclosure will be described more fully below (e.g., with reference to the accompanying drawings). Like reference numerals may refer to like elements throughout the specification and drawings.

Generally, in the flexible waveguide described herein (e.g., flexible waveguides 301, 401, 801, 1001, 1201, 1301, 1401 and 1501), the ultrasonic waveguide is thinned down enough at articulating portions thereof (e.g., articulating portions 310, 410, 430, 810, 1010, 1210, 1310, 1410, 1510, 1747 and 1748) to be elastically flexible, but still has enough material to carry the ultrasonic wave to the tip of the instrument (e.g. to end effectors 100, 200, 600, 700, and 1700). While the flexible waveguide has a substantially cylindrical shape, the thinned down and elastically flexible sections may be at least partially flattened to create an at least partially flattened shape, e.g., including opposed planar surfaces. The thinned down and elastically flexible sections may also have round or elliptical cross sections. The term "flattened" relates to the end configuration and not the method of achieving the flexible section(s). The above configuration enables an articulating ultrasonic surgical instrument wherein the ultrasonic transducer would be "outside" the body and the ultrasonic wave would be carried through the flex in the waveguide to the end effector.

End effectors 100, 200, 600, 700, and 1700 described herein are substantially the same as each other unless otherwise indicated. Flexible waveguides 301, 401, 801, 1001, 1201, 1301, 1401 and 1501 described herein are substantially the same as each other, unless otherwise indicated. Articulating portions 310, 410, 430, 810, 1010, 1210, 1310, 1410, 1510, 1747 and 1748 described herein are substantially the same as each other, unless otherwise indicated. Jaw members 101, 201, 601, 701, 1601, 1701, 2001, 2201, 2601 and 2701 described herein are substantially the same as each other, unless otherwise indicated. Blade members 102, 202, 602, 702, 1602, 1702, 2002, 2502, 2602 and 2702 described herein are substantially the same as each other, unless otherwise indicated. Housings 12 and 212 as described herein are substantially the same as each other, unless otherwise indicated. Handle assemblies 132 and 232 described herein are substantially the same as each other, unless otherwise indicated. Stabilizers 351 and 851 described herein are substantially the same as each other, unless otherwise indicated. Stabilizers 352 and 852 described herein are substantially the same as each other, unless otherwise indicated.

Referring generally to FIG. 1, an embodiment of a surgical instrument (e.g., an endoscopic surgical instrument) exemplifying the aspects and features of the present disclosure is shown generally identified by reference numeral 10. For the purposes herein, surgical instrument 10 is generally described. Aspects and features of surgical instrument 10 not germane to the understanding of the present disclosure are omitted to avoid obscuring the aspects and features of the present disclosure in unnecessary detail.

Surgical instrument 10 generally includes a housing 12 (defining a handle assembly 132), an elongated body 14, and an end effector 100. Handle assembly 132 supports a battery assembly 18 and a transducer and generator assembly ("TAG") 120, and includes a first rotation knob 22, a second rotation knob 23, an activation button 24, and a clamp trigger 26.

Elongated body 14 defines a proximal end portion 16 connected with the first rotation knob 22 and a distal end portion 18 supporting end effector 100. End effector 100 includes an ultrasonic blade 102 and a pivoting jaw 101. In embodiments, ultrasonic blade 102 is cylindrical or otherwise includes one or more radial symmetries (or is fully radially symmetric) and jaw 101 is configured to rotate about the ultrasonic blade 102 to enable clamping tissue therebetween at plural (or an infinite number of) orientations. A lumen 15 is defined within elongated body 14.

Clamp trigger 26 of surgical instrument 10 is selectively manipulatable to actuate a motor, other powered drive mechanism, or a manual drive mechanism, e.g., gears, pulleys, tension cables, etc., to pivot jaw 101 relative to ultrasonic blade 102 to thereby transition end effector 100 between an open condition and a clamping condition.

First rotation knob 22 is selectively manipulatable to rotate elongated body 14 and, thus, end effector 100 relative to housing 12. Second rotation knob 23 is selectively manipulatable to actuate a motor, other powered drive mechanism, or a manual drive mechanism, e.g., gears, pulleys, tension cables, etc., to rotate jaw member 101 relative to ultrasonic blade 102. As an alternative to first and second rotation knobs 22, 23, other suitable actuation mechanism, e.g., toggle switches, joysticks, buttons, etc., may be provided. Third rotation knob 127 is selectively manipulatable to articulate articulating portion 110.

Battery assembly 18 and the generator of TAG 120 cooperate, upon activation of activation button 24, to supply power to the transducer of TAG 120 to enable the generation of ultrasonic energy that is transmitted to blade 102 of end effector 100 for treating tissue therewith, e.g., to coagulate, cauterize, fuse, seal, cut, desiccate, or otherwise treat tissue, as detailed below. Battery assembly 18 and TAG 20 are each releasably secured to handle assembly 132, and are removable therefrom to facilitate disposal of handle assembly 132, with the exception of battery assembly 18 and TAG 120. However, it is contemplated that any or all of the components of surgical instrument 10 be configured as disposable single-use components or sterilizable multi-use components, and/or that surgical instrument 10 be connectable to a remote power source or generator rather than having such components on-board.

Referring particularly to FIGS. 1, 3, 6A, 6B, and 7A-7D, surgical instrument 10, as noted above, includes housing 12 and elongated body 14 extending therefrom. Elongated body 14 defines a lumen 15 therein, a proximal end portion 16 and a distal end portion 18 supporting end effector 100. Elongated body 14 includes at least one articulating portion 110 between the proximal end portion 16 and the distal end portion 18. A flexible waveguide (e.g. flexible waveguide 301 of FIG. 3) extends through lumen 15 and includes an articulating portion 310. The articulating portion 110 of elongated body 14 and the articulating portion 310 of flexible waveguide are positioned in substantially a same location along the elongated body 14 such that articulating portion 110 and articulating portion 310 can articulate in a similar manner as each other. Elongated body 14 is configured to rotate in unison with flexible waveguide 310 extending through lumen 15 and jaw member 101 is configured to rotate about blade 102 (see also, e.g., jaw member 601 and blade 602 FIGS. 6A and 6B). Thus, surgical instrument 10 can achieve any desired directional orientation for end effector 100 through a combination of rotating elongated body 14, articulation of articulating portions 110 and 310, and rotating jaw member 101 about blade 102 (see also, e.g., elongated body 714, articulation portion 730, jaw member 701, and blade 702 of FIGS. 7A to 7D). This may be achieved with a single articulating region along elongated body 14, or with multiple articulating regions.

Figure 3:
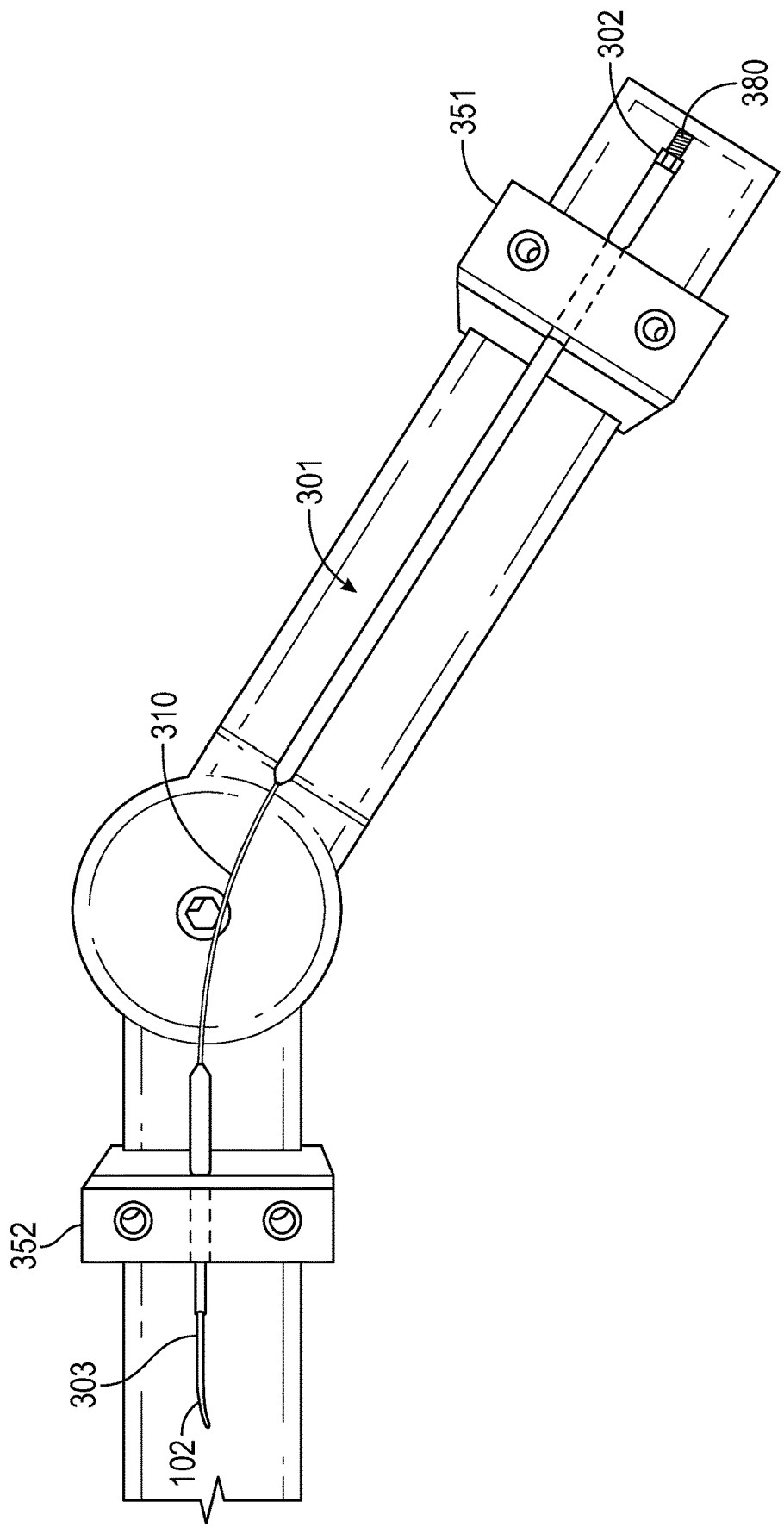
FIG. 3 is a side view of a single conceptualized articulating portion including a flexible waveguide shown restrained in a test fixture representing support, pivot, and other features, the flexible waveguide configured for use with the surgical instrument of FIG. 1.
Figure 4A:
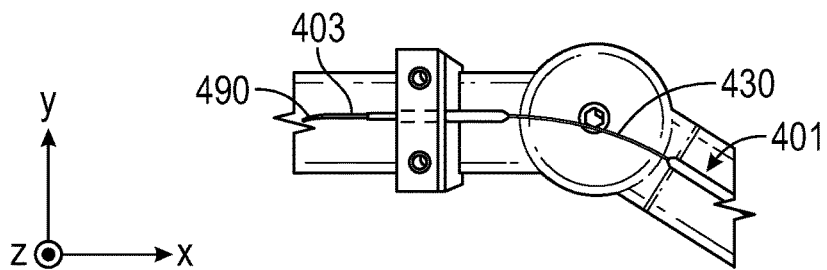
FIG. 4A is a side view of a conceptualized first articulating portion including a first portion of a flexible waveguide shown restrained in a test fixture representing support, pivot, and other features, the flexible waveguide configured for use with the surgical instrument of FIG. 2 articulated in a first plane.
Figure 4B:
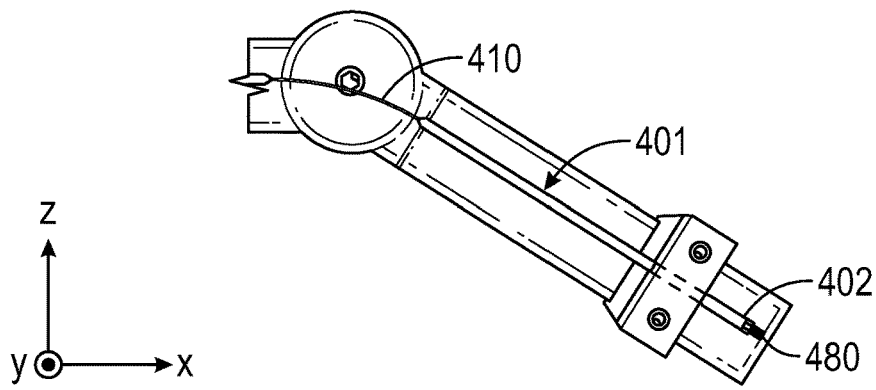
FIG. 4B is a side view of a conceptualized second articulating portion including a second portion of a flexible waveguide shown restrained in a test fixture representing support, pivot, and other features, the flexible waveguide configured for use with the surgical instrument of FIG. 2, articulated in a second plane.

Referring to FIGS. 1 and 3, flexible waveguide 301 extends through the lumen 15 of the elongated body 14. A proximal end portion 302 of the flexible waveguide 301 is connected with the ultrasonic generator 120. A distal end portion 303 of the flexible waveguide 301 is connected, e.g., attached, formed integrally with, etc., to the blade 102 of the end effector 100. The flexible waveguide 301 defines the articulating portion 310 having a narrower dimension, e.g., width, than other portions of the flexible waveguide 301. In this manner, the articulating portion 310 is flexible while the remainder of waveguide 301 is substantially inflexible (e.g., not configured to significantly flex during use). Proximal end portion 302 may define a threaded end 380 for connecting with ultrasonic generator 120 and distal end portion 303 may define blade 102.

The articulating portion including articulation portion 110 of elongated body 14, and articulating portion 310 of waveguide 301 may enable articulation relative to a single plane defined by the thinned portion (articulating portion 310) of the flexible waveguide 301. Blade 102, as noted above, is cylindrical or otherwise defines one or more radial symmetries and rotatable jaw 101 is rotatable about blade 102. The blade 102 may have a curved or partially curved configuration (see, e.g., FIG. 3) or a substantially straight configuration (see, e.g., FIG. 6B). By making the blade 102 cylindrical or otherwise defining one or more radial symmetries, it allows for clamping jaw 101 on the blade 102 at plural points or any point on an outer surface thereof while allowing for achievement of the same tissue effect. The flexible waveguide 301 is substantially cylindrical along a majority of the length thereof, and further includes articulating portion 310 having a partially flattened shape. Because of the cylindrical portion of the waveguide, the jaw 101 can rotate around the blade 102, while the blade 102 is stationary.

Referring to FIGS. 2, 4A, 4B, 5A, and 5B, surgical instrument 20 is substantially the same as surgical instrument 10, except for having a first articulating portion 210 and a second articulating portion 230. Each articulating portion 210 and 230 may achieve a somewhat gentle bend (e.g., from about 1 degree to about 45 degrees) about a single plane (e.g., a single or a different plane from each other). Surgical instrument 20 generally includes a housing 212 (defining a handle assembly 232), an elongated body 214 defining a proximal end portion 216 and a distal end portion 218 and a lumen 215 therein, and an end effector 200. End effector 200 includes an ultrasonic blade 202 and a jaw 201 pivotable relative to ultrasonic blade 202 and that may be configured to rotate about the ultrasonic blade 202. Handle assembly 232 supports a battery assembly 218 and a transducer and generator assembly ("TAG") 220, and includes a first rotation knob 222, a second rotation knob 223, an activation button 224, a clamp trigger 226, a third rotation knob 227 and a fourth rotation knob 228.

Flexible waveguide 401 including first articulating portion 410 and second articulating portion 430 extending through lumen 215 of elongated body 214. The first articulating portion 210 of elongated body 214 and the first articulating portion 410 of flexible waveguide 401 are positioned in substantially a same location as each other along the elongated body 214 such that first articulating portion 210 and first articulating portion 410 can articulate in a similar manner as each other. The second articulating portion 230 of elongated body 214 and the second articulating portion 430 of flexible waveguide 401 are positioned in substantially a same location as each other along the elongated body 214 such that second articulating portion 230 and second articulating portion 430 can articulate in a similar manner as each other, e.g., in a second plane different from a plane of articulation of the first portions 210, 410. Alternatively, the second plane may be substantially the same as the first plane (e.g., the first and second planes may each be along the Y-Axis direction of FIGS. 4A, 4B, 5A, and 5B). For example, the first plane may be along the Y-axis direction of FIGS. 4A, 4B, 5A, and 5B and the second plane may be along the Z-axis direction of FIGS. 4A, 4B, 5A, and 5B. Thus, elongated member 214 and the flexible waveguide 401 extending therethrough may articulate about two different directions to achieve a desired directional orientation of end effector 200 and/or to achieve desired placement of various segments of elongated member 214.

Figure 5A:
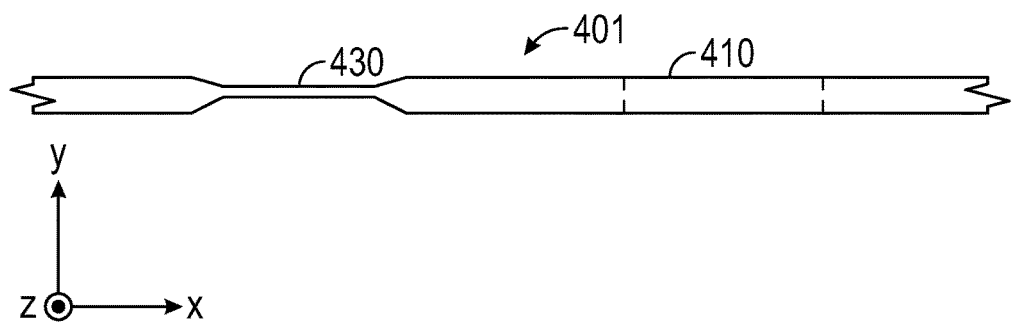
FIG. 5A is a side view of the flexible waveguide of FIG. 4A.
Figure 5B:
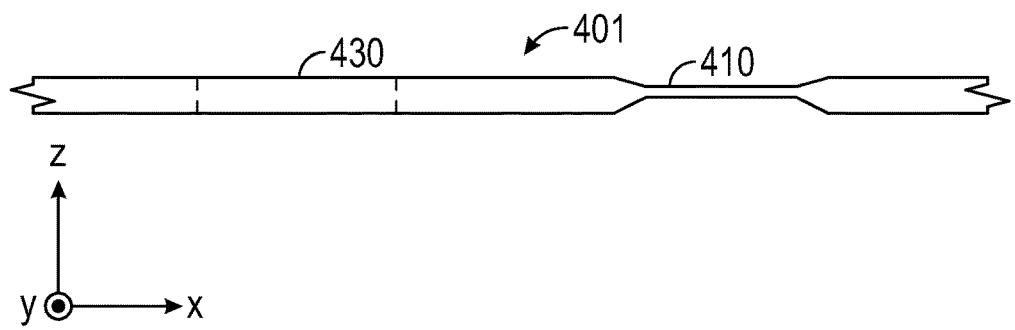
FIG. 5B is a top plan view of the flexible waveguide of FIG. 4A.

Referring particularly to FIGS. 5A and 5B, because the articulating portions 410, 430 of flexible waveguide 401 are formed to have flattened shapes, the thinning of articulation portion 430 of flexible waveguide 401 might only be visible about a single plane (e.g., a side view as in FIG. 5A), while the thinning of articulation portion 410 of flexible waveguide 401 might only be visible about a different single plane (e.g., a plan view as in FIG. 5B).

Figure 8:
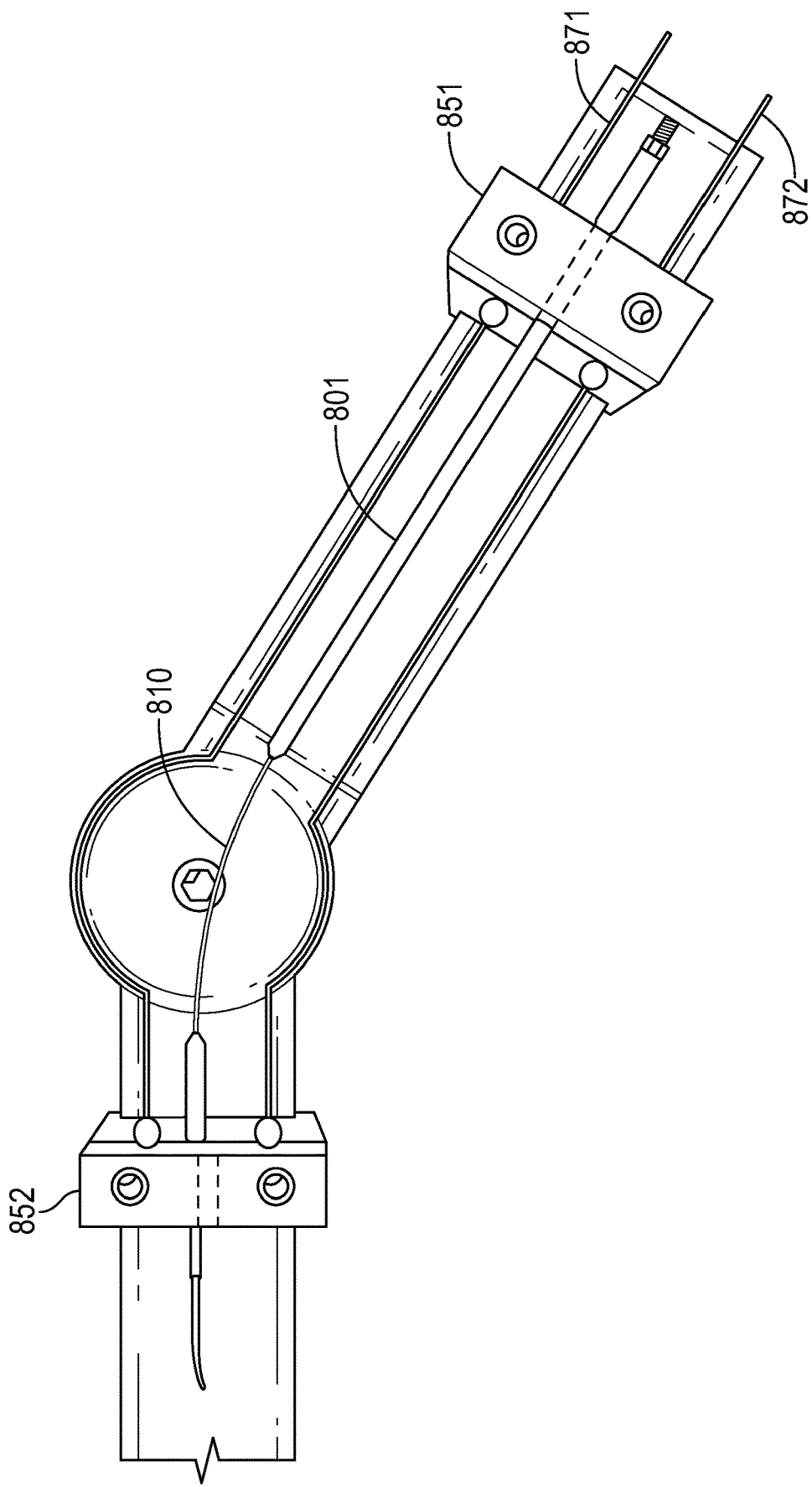
FIG. 8 is a side view of a conceptualized articulation portion including a cable system for articulating the articulating portion and the flexible waveguide, the flexible waveguide shown restrained in a test fixture representing support, pivot, and other features and configured for use with the surgical instrument of FIG. 1 or 2.

Referring particularly to FIG. 8, a cable system including first cable 871 and second cable 872 may be employed for articulating an articulating portion 810 of a flexible waveguide 801. While two cables may be employed, a single cable on a spool may also be employed or more than two cables may be utilized. The cables 871, 872 may route beside the flexible waveguide 801 within a lumen (e.g., lumen 15 or 215 described herein (FIGS. 1 and 2, respectively)). By pulling on one cable 871, 872, and releasing slack in the other cable 871, 872, the articulating portion 810 is urged to articulate in the direction of the tensioned cable. Alternatively, articulating the articulating portion 810 of the flexible waveguide 801 may be achieved by use of a thin wire of nitinol or other material, to push and pull on an inner tube of the elongated portion for flexing actuation. The thin wire may be held in a sleeve or channel to allow for pushing, without buckling. The inner lumen described is employed to house the flexible waveguide 801, while the cable systems and the like described herein employ cables or similar apparatus housed within separate lumens or channels to maintain separation from the flexible waveguide 801.

Referring particularly to FIGS. 3 and 8, stabilizers 351, 851 and 352, 852 may be employed for assisting in the controlled articulation of the flexible waveguide 301, 801. The stabilizers 351, 851 are secured to the flexible waveguide 301, 801 at positions proximal and distal of the articulating portions 310, 810 of the flexible waveguide 301, 801. The stabilizers 351, 851 and 352, 852 may be secured to an inner surface of the elongated member described herein. Thus, proximal/distal movement of the flexible waveguide 301, 801 is inhibited. Holding/stabilizing the flexible waveguide 301, 801 at these locations allows formation of a gradual bend of articulation, without causing a heating/friction point or causing unnecessary noise in the flexible waveguide 301, 801. Although FIGS. 3 and 8 conceptually illustrate elongated bodies including stabilizers 351, 851 holding/stabilizing the flexible waveguides 301, 801, a person of skill in the art would readily appreciate how such stabilizers would, in practice, be incorporated into elongated body 14 (FIG. 1), for holding/stabilizing flexible waveguides 301, 801 therein. Additional stabilizing structures for the flexible waveguide 301, 801 are described below with reference to FIGS. 12A to 15D.

Figure 6B:
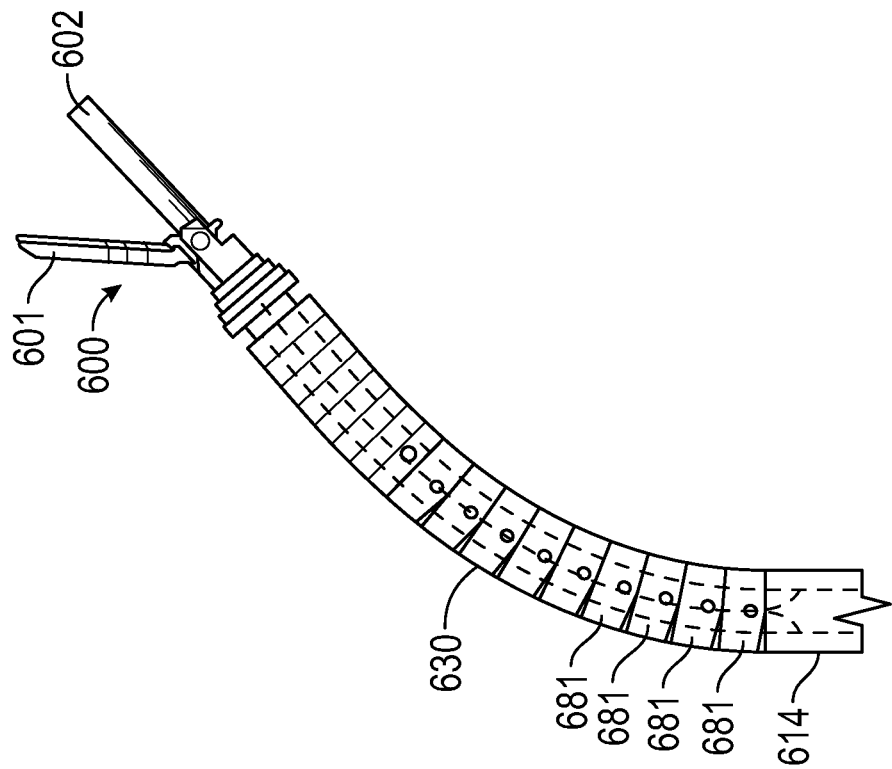
FIG. 6B is a side view of the distal end of the elongated body, and the end effector of FIG. 6A in a second rotational position.
Figure 6A:
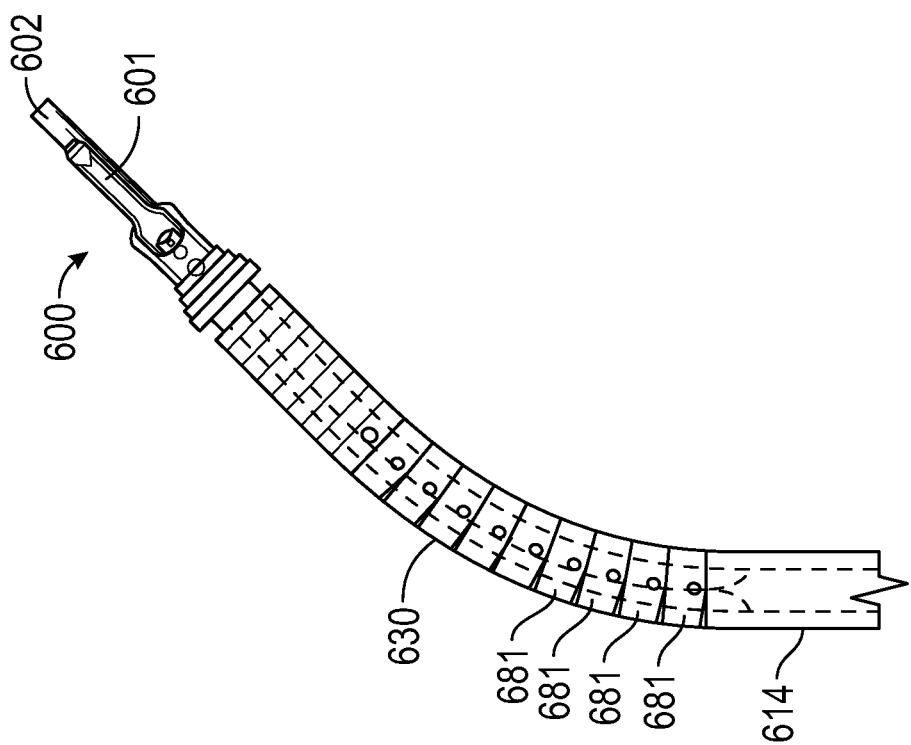
FIG. 6A is a side view of a distal end of an elongated body, and end effector including a rotatable jaw member, configured for use with the surgical instrument of FIG. 1 or 2 in a first rotational position.
Figures 7A, 7B:
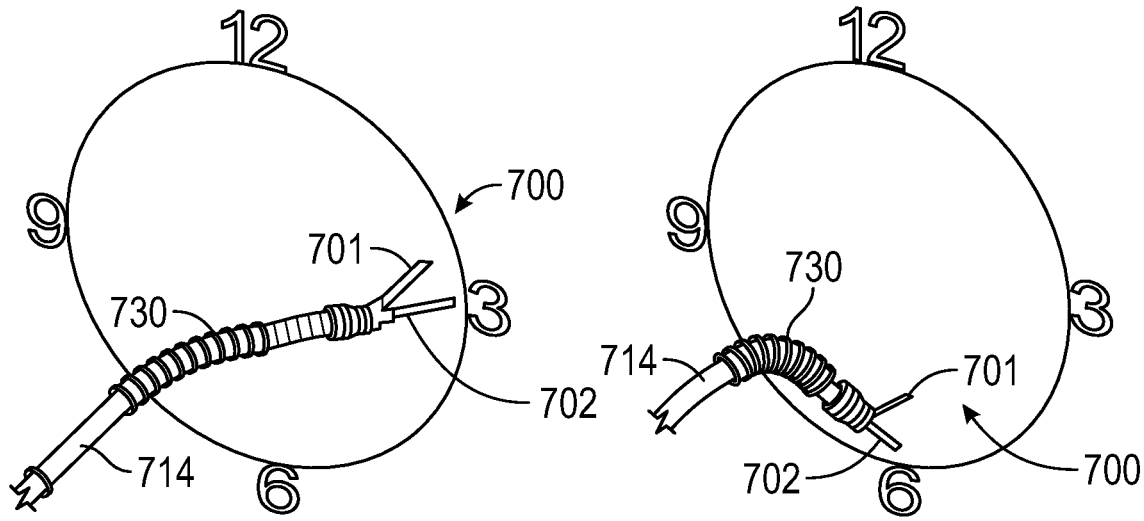
FIGS. 7A-7D are side, perspective views of the elongated body, and end effector including a rotatable jaw member, of FIG. 6A, in various rotational and articulated orientations.
Figures 7C, 7D:
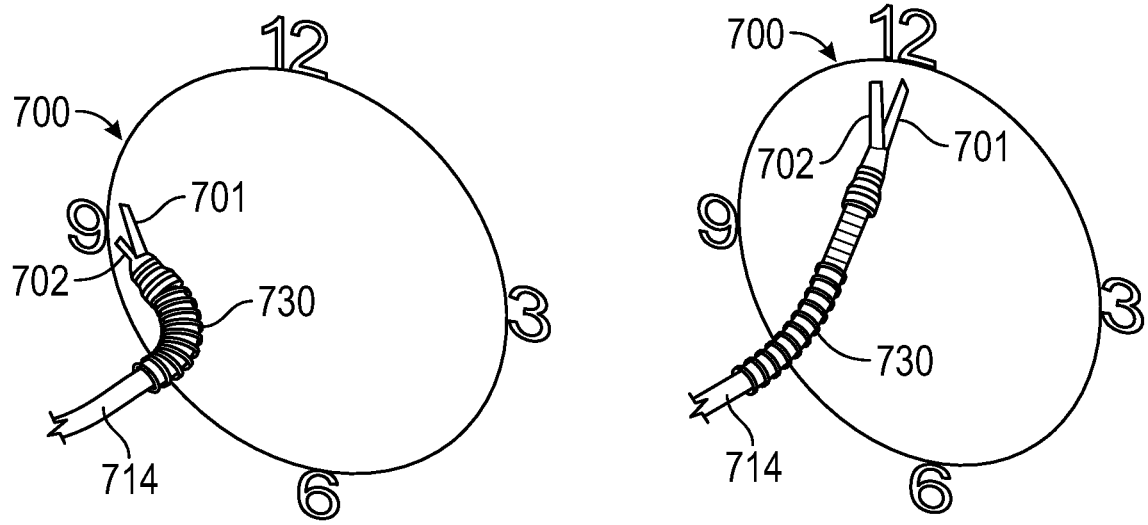
Figure 9:
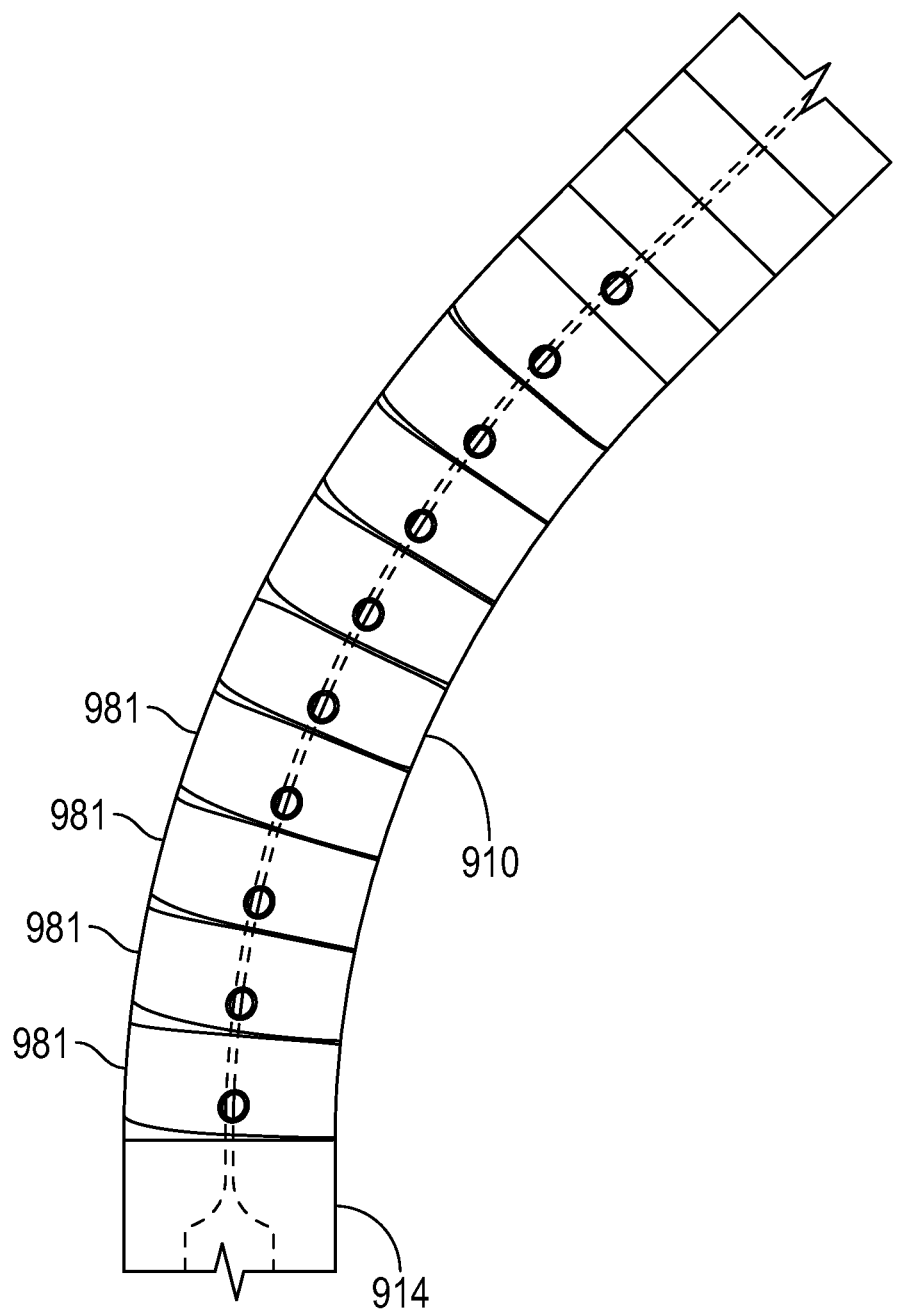
FIG. 9 is a side view of another articulating portion configured for use with the elongated body of the surgical instrument of FIG. 1 or 2 having a plurality of flexing sections.

Referring particularly to FIGS. 6A, 6B and 9, articulating portions 630, 910 of elongated bodies 614, 914 may include a plurality of flexing sections 681, 981 to control a degree of articulation of articulating portions 630, 910. The flexing sections 681, 981 allowing a gentle bend to be achieved by only allowing a certain amount of flex per section. As an example, each flexing sections 681, 981 may allow about 5 degrees of flex, thus using 9 flexing sections 681, 981 allows about 45 degrees total of bend. The flexing sections 681, 981 may only allow bend in one plane, by means of a pinned joint or hinge or partial cuts, or may be configured to bend in multiple planes.

Referring generally to FIGS. 2 and 4A, 4B, 5A, and 5B again, the surgical instrument 20 includes a housing 212 having the elongated body 214 extending distally therefrom. The elongated body 214 defines the first articulating portion 210 and the second articulating portion 230 distal of the first articulating portion 210. The elongated body 214 defines lumen 215 therein. End effector 200 is supported at distal end portion 218 of the elongated body 214. Ultrasonic transducer and generator assembly 220 is supported on the housing 212. Flexible waveguide 401 extends within the lumen 215 of the elongated body 214. Proximal end portion 480 of the flexible waveguide 401 is connected with the ultrasonic generator 220. Distal end portion 490 of the flexible waveguide 401 is connected with (attached to, integrally formed with, etc.) the blade 202 of the end effector 200. The flexible waveguide 401 defines first articulating portion 410 having a narrower dimension, e.g., width, than a width of other portions of the flexible waveguide 401. The flexible waveguide 401 defines second articulating portion 430 configured to articulate in a different direction (e.g., about the Z-axis direction of FIG. 4B) from the articulating direction of the first articulating portion 410 (e.g., about the Y-axis direction of FIG. 4A). Second articulating portion 430 has a different narrower dimension (as compared to first articulating portion 410), e.g., a narrowed height, than a height of other portions of the flexible waveguide 401.

The end effector 200 includes ultrasonic blade 202, which may be cylindrical or otherwise define one or more radial symmetries, and jaw 201, which may be configured to rotate about the ultrasonic blade 202. The ultrasonic blade 202 and the jaw 201 are configured to capture and treat tissue therebetween in a clamping position of jaw 201. Alternatively or additionally, ultrasonic blade 202 may be utilized to treat unclamped tissue in close proximity therewith. The elongated body 214 is configured to rotate (see, e.g., elongated body 614 of FIGS. 6A and 6B) to achieve different directional orientations of end effector 200.

The first rotation knob 222 is configured to rotate the elongated body 214 (e.g., to rotate the portion of the elongated body 214 proximal to the first articulating portion 210). The second rotation knob 223 is configured to rotate the jaw 201 about the ultrasonic blade 202, in embodiments where such rotation is provided. The third rotation knob 227 is configured to articulate the first articulating portion 210 of the elongated body 214 and, thus, the first articulating portion of the waveguide 410. The fourth rotation knob 228 is configured to articulate the second articulating portion 230 of the elongated body 214 and, thus, the second articulating portion 430 of the flexible waveguide.

Figure 10:
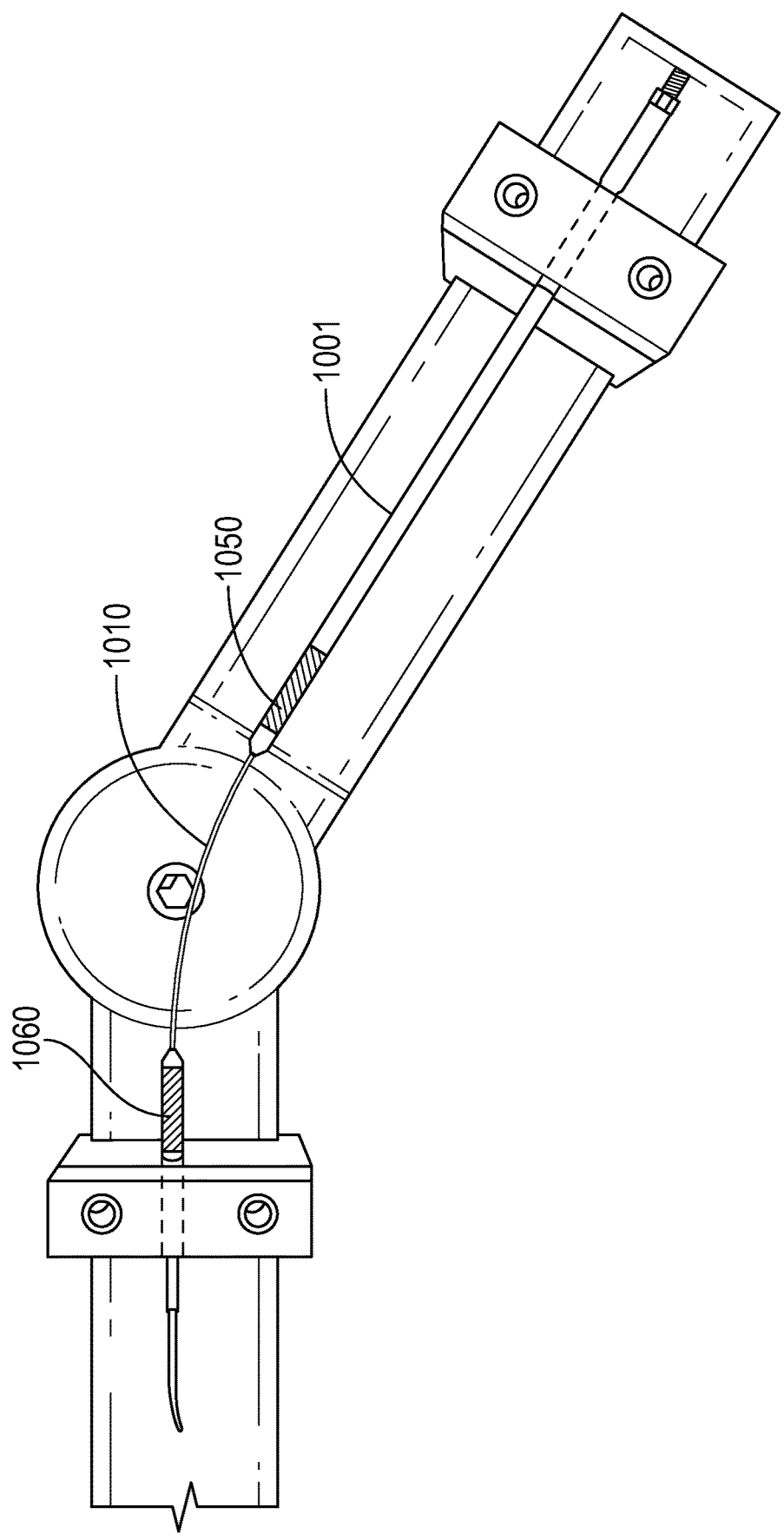
FIG. 10 is a side view of a conceptualized articulation portion including a flexible waveguide shown restrained in a test fixture representing support, pivot, and other features, the flexible waveguide configured for use with the surgical instrument of FIG. 1 or 2 and including transducers positioned at opposite sides of the articulating portion of the flexible waveguide.

Referring to FIG. 10, a first transducer 1050 and a second transducer 1060 are positioned at opposite sides, e.g., proximally and distally, of an articulating portion 1010 of a flexible waveguide 1001. The first and second transducers 1050 and 1060 amplify an ultrasonic wave transmitted through the articulating portion 1010 of the flexible waveguide 1001, e.g., the portion having the narrower width than the width of other portions of the flexible waveguide 1001. For example, the second transducer 1060 distal of the articulating portion 1010 amplifies the ultrasonic energy as the wave continues down the waveguide (i.e., makes up for any loss in energy resulting from the articulating portion 1010). In embodiments, only the transducer distal of articulation portion 1010, e.g., second transducer 1060, is provided. Similar transducers may be positioned at opposite sides (or only on the distal side) of each articulating portion of a flexible waveguide having multiple articulating portions along a length thereof.

The various embodiments disclosed herein may also be configured to work with robotic surgical systems and what is commonly referred to as "Telesurgery." Such systems employ various robotic elements to assist the surgeon and allow remote operation (or partial remote operation) of surgical instrumentation. Various robotic arms, gears, cams, pulleys, electric and mechanical motors, etc. may be employed for this purpose and may be designed with a robotic surgical system to assist the surgeon during the course of an operation or treatment. Such robotic systems may include remotely steerable systems, automatically flexible surgical systems, remotely flexible surgical systems, remotely articulating surgical systems, wireless surgical systems, modular or selectively configurable remotely operated surgical systems, etc.

The robotic surgical systems may be employed with one or more consoles that are next to the operating theater or located in a remote location. In this instance, one team of surgeons or nurses may prep the patient for surgery and configure the robotic surgical system with one or more of the instruments disclosed herein while another surgeon (or group of surgeons) remotely controls the instruments via the robotic surgical system. As can be appreciated, a highly skilled surgeon may perform multiple operations in multiple locations without leaving his/her remote console which can be both economically advantageous and a benefit to the patient or a series of patients.

The robotic arms of the surgical system are typically coupled to a pair of master handles by a controller. The handles can be moved by the surgeon to produce a corresponding movement of the working ends of any type of surgical instrument (e.g., end effectors, graspers, knifes, scissors, etc.) which may complement the use of one or more of the embodiments described herein. The movement of the master handles may be scaled so that the working ends have a corresponding movement that is different, smaller or larger, than the movement performed by the operating hands of the surgeon. The scale factor or gearing ratio may be adjustable so that the operator can control the resolution of the working ends of the surgical instrument(s).

The master handles may include various sensors to provide feedback to the surgeon relating to various tissue parameters or conditions, e.g., tissue resistance due to manipulation, cutting or otherwise treating, pressure by the instrument onto the tissue, tissue temperature, tissue impedance, etc. As can be appreciated, such sensors provide the surgeon with enhanced tactile feedback simulating actual operating conditions. The master handles may also include a variety of different actuators for delicate tissue manipulation or treatment further enhancing the surgeon's ability to mimic actual operating conditions.

Figure 11:
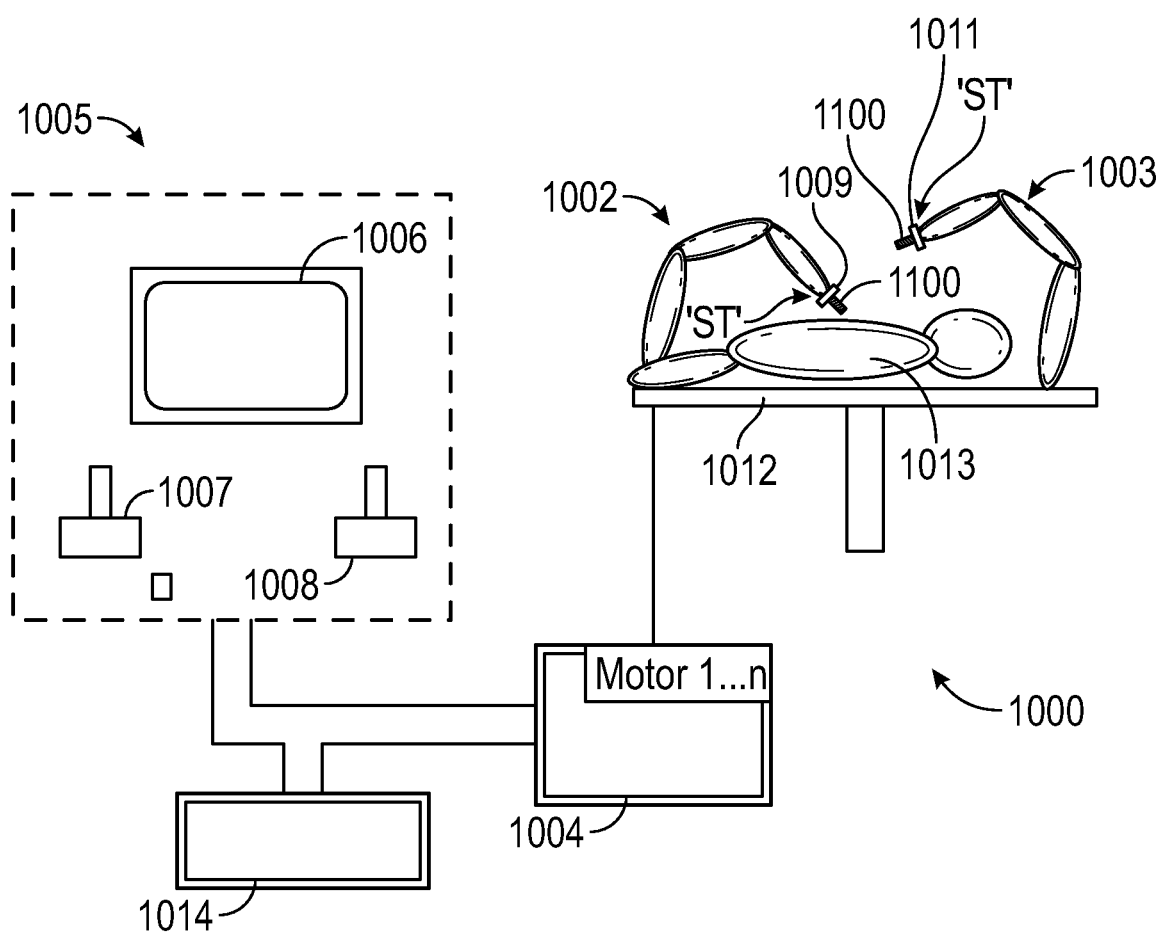
FIG. 11 is a schematic illustration of a robotic surgical system configured for use in accordance with the present disclosure.
Figure 12A:
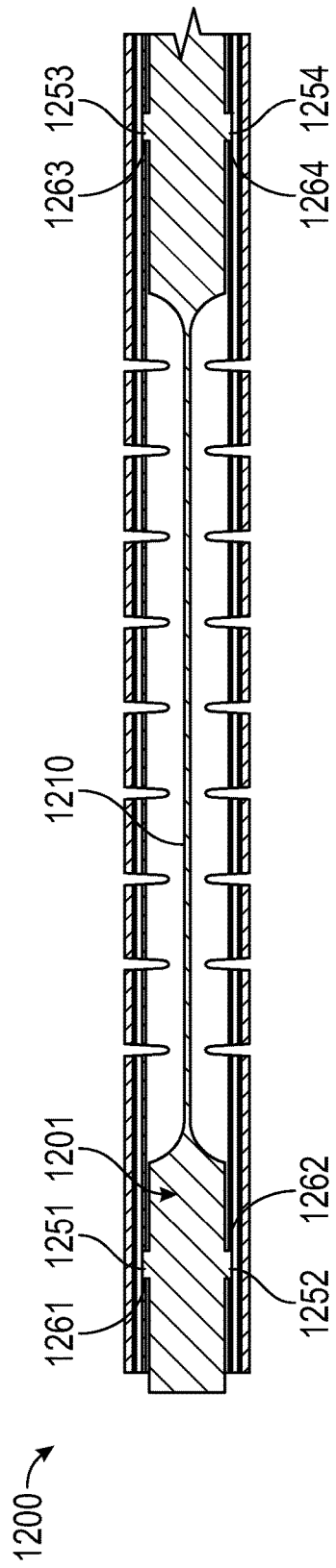
FIG. 12A is a longitudinal, cross-sectional view of a flexible waveguide secured within a lumen of an elongated body by a post and hole attachment structure.
Figure 12B:
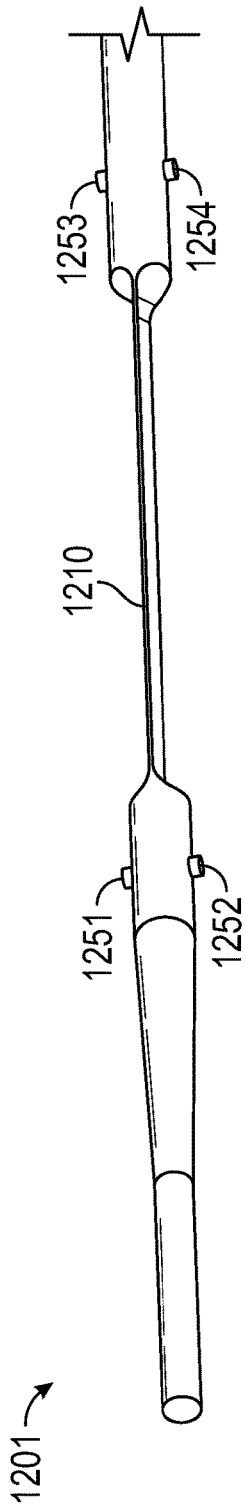
FIG. 12B is a perspective view of the flexible waveguide of FIG. 12A.
Figure 12C:
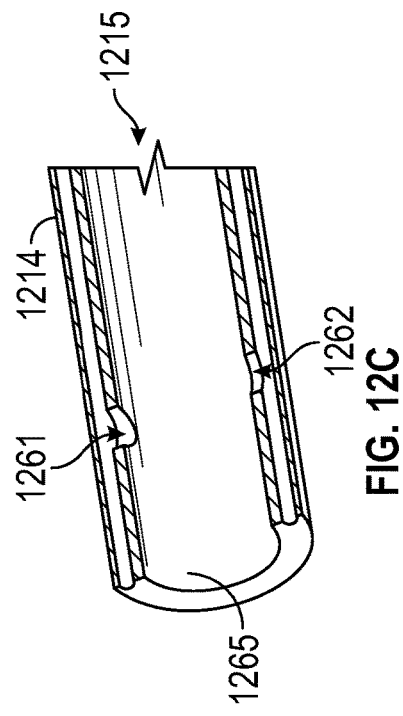
FIG. 12C is a longitudinal, cross-sectional view of the holes formed in an inner surface of the elongated body of FIG. 12A.
Figure 12D:
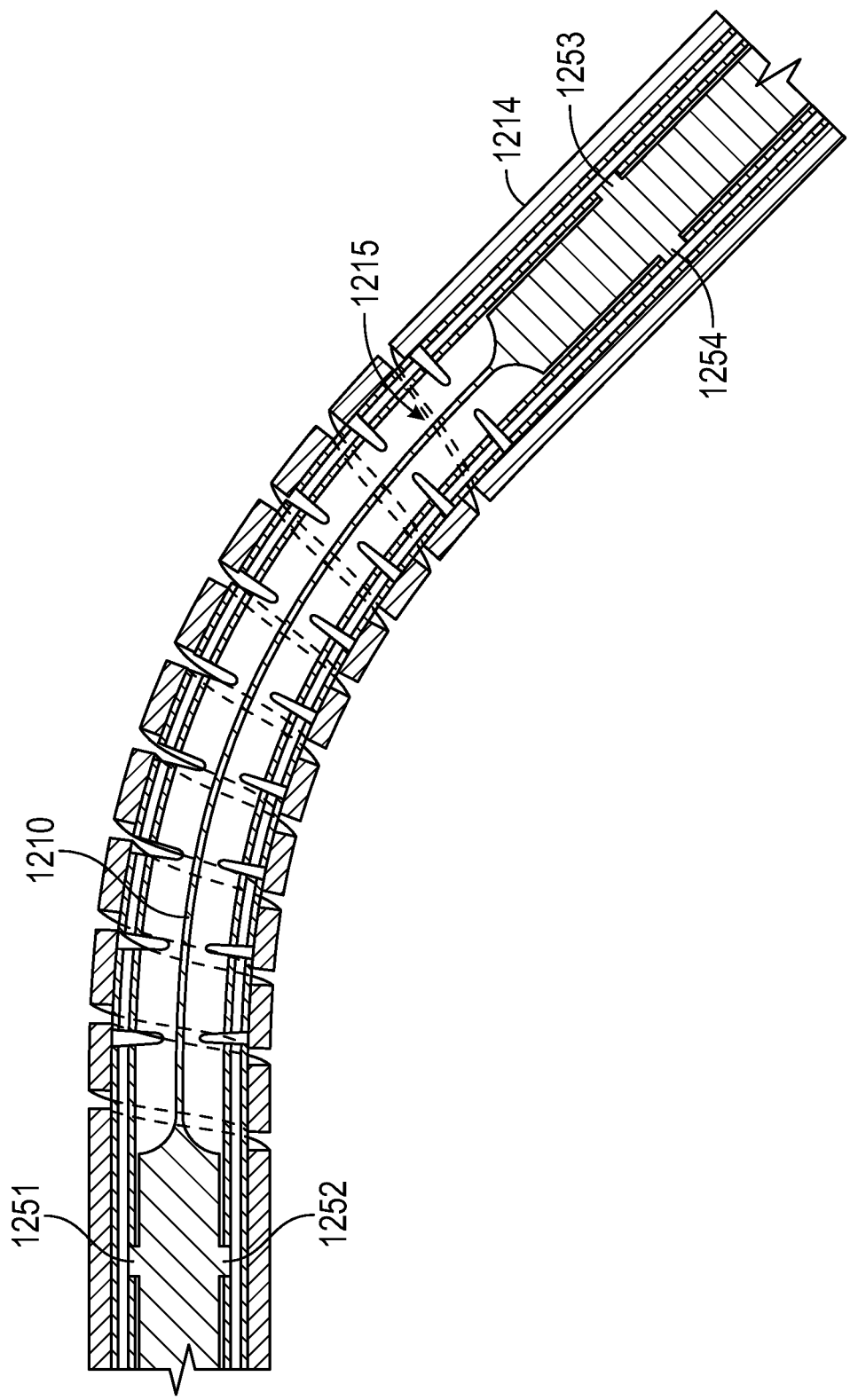
FIG. 12D is a longitudinal, cross-sectional view of the elongated body and the flexible waveguide of FIG. 12A in an articulated configuration.

FIG. 11 illustrates a medical work station shown generally as work station 1000 and generally may include a plurality of robot arms 1002, 1003; a control device 1004; and an operating console 1005 coupled with control device 1004. Operating console 1005 may include a display device 1006, which may be set up in particular to display three-dimensional images; and manual input devices 1007, 1008, by means of which a person (not shown), for example a surgeon, may be able to telemanipulate robot arms 1002, 1003 in a first operating mode.

Each of the robot arms 1002, 1003 may include a plurality of members, which are connected through joints, and an attaching device 1009, 1011, to which may be attached, for example, a surgical tool "ST" supporting an end effector 1100, in accordance with any one of several embodiments disclosed herein, as will be described in greater detail below. In embodiments, end effector 1100 may include, for example the elongated body (or portion thereof) and end effector of any of the embodiments detailed therein; thus, robot arm 1003 (together with relevant portions of control device 1004, operating console 1005, and/or manual input devices 1007, 1008) functions are the housings 12, 212 (FIGS. 1 and 2, respectively) of the ultrasonic surgical instrument.

Robot arms 1002, 1003 may be driven by electric drives (not shown) that are connected to control device 1004. Control device 1004 (e.g., a computer) may be set up to activate the drives, in particular by means of a computer program, in such a way that robot arms 1002, 1003, their attaching devices 1009, 1011 and thus the surgical tool (including end effector 1100) execute a desired movement according to a movement defined by means of manual input devices 1007, 1008. Control device 1004 may also be set up in such a way that it regulates the movement of robot arms 1002, 1003 and/or of the drives.

Medical work station 1000 may be configured for use on a patient 1013 lying on a patient table 1012 to be treated in a minimally invasive manner by means of end effector 1100. Medical work station 1000 may also include more than two robot arms 1002, 1003, the additional robot arms likewise being connected to control device 1004 and being telemanipulatable by means of operating console 1005. A medical instrument or surgical tool (including an end effector 1100) may also be attached to the additional robot arm. Medical work station 1000 may include a database 1014, in particular coupled to with control device 1004, in which are stored, for example, pre-operative data from patient/living being 1013 and/or anatomical atlases.

Referring particularly to FIGS. 12A to 12D, a support system 1200 for flexible waveguide 1201 is described. The flexible waveguide 1201 includes a plurality of protruding posts 1251, 1252, 1253, 1254 extending from the flexible waveguide 1201. The protruding posts 1251 and 1252 are shaped and dimensioned to be received in corresponding recesses 1261 and 1262, respectively. Protruding posts 1253 and 1254 are similarly received in corresponding recesses 1263 and 1264, respectively. The recesses 1261 and 1262 are formed in an inner surface 1265 of elongated member 1214 and are configured to receive the protruding posts 1253 and 1254, respectively, therein to secure the flexible waveguide 1201 within lumen 1215 of elongated member 1214. Some of the plurality of protruding posts 1251, 1252, 1253, 1254 are positioned proximally of articulating portion 1210 and others of the plurality of protruding posts 1251, 1252, 1253, 1254 are positioned distally of articulating portion 1210 to allow articulation of the articulating portion 1210 within lumen 1215 and to prevent contact between articulating portion 1210 and the inner surface 1265 of elongated member 1214 (see, e.g., FIG. 12D).

Figure 13A:
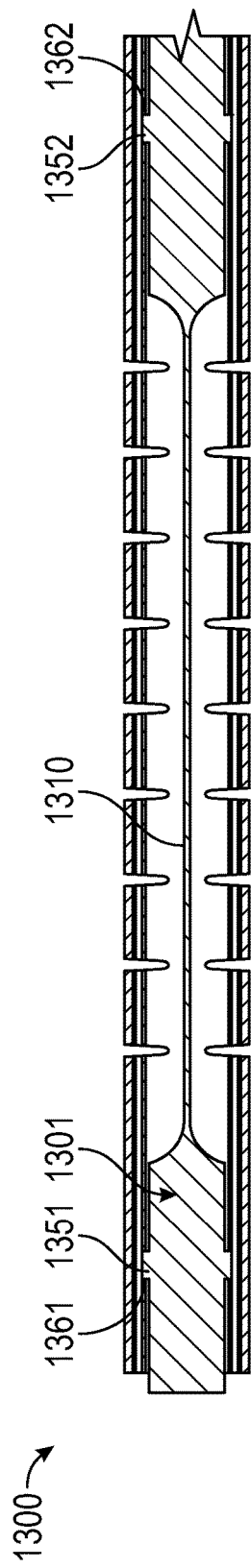
FIG. 13A is a longitudinal, cross-sectional view of a flexible waveguide secured within a lumen of an elongated body by an annular collar protruding outwardly from the flexible waveguide.
Figure 13B:
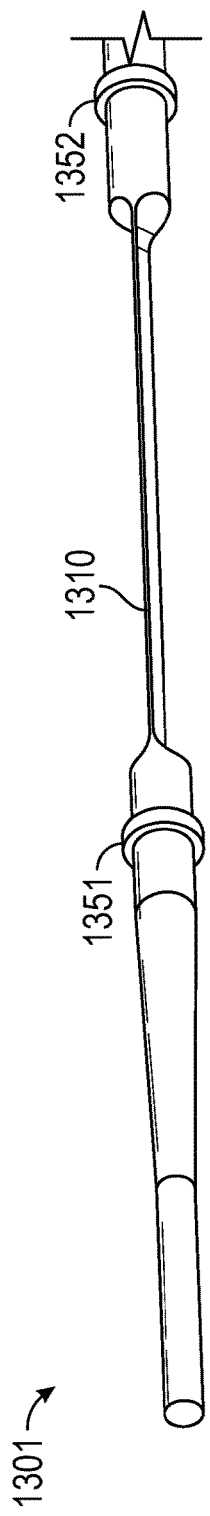
FIG. 13B is a perspective view of the flexible waveguide of FIG. 13A.
Figure 13C:
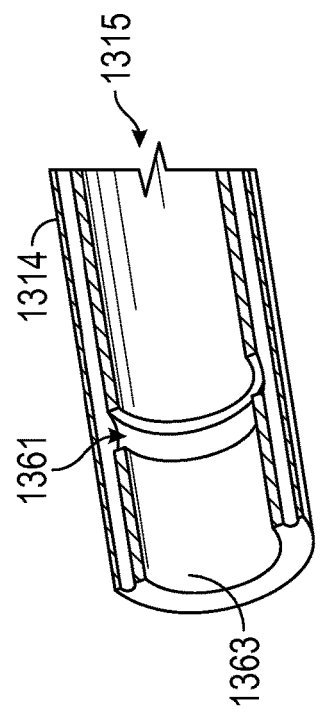
FIG. 13C is a longitudinal, cross-sectional view of a recess formed in an inner surface of the elongated body and configured to receive the annular collar of FIG. 13A.

Referring particularly to FIGS. 13A to 13C, a support system 1300 for flexible waveguide 1301 is described. The flexible waveguide 1301 includes a first annular collar 1351 and a second annular collar 1352 circumferentially protruding from the flexible waveguide 1301. first and second annular collars 1351 and 1352 are shaped and dimensioned to be received in a corresponding recess 1361, 1362, respectively. The recesses 1361 and 1362 are circumferentially formed in an inner surface 1363 of elongated member 1314 and are configured to receive the annular collars 1351 and 1352, respectively, therein to secure the flexible waveguide 1301 within lumen 1315 of elongated member 1314. The annular collars 1351, 1352 and recesses 1361, 1362 are positioned proximally and distally, respectively, of articulating portion 1310 to allow articulation of the articulating portion 1310 within lumen 1315 and to prevent contact between articulating portion 1310 and the inner surface 1363 of elongated member 1314.

Figure 14A:
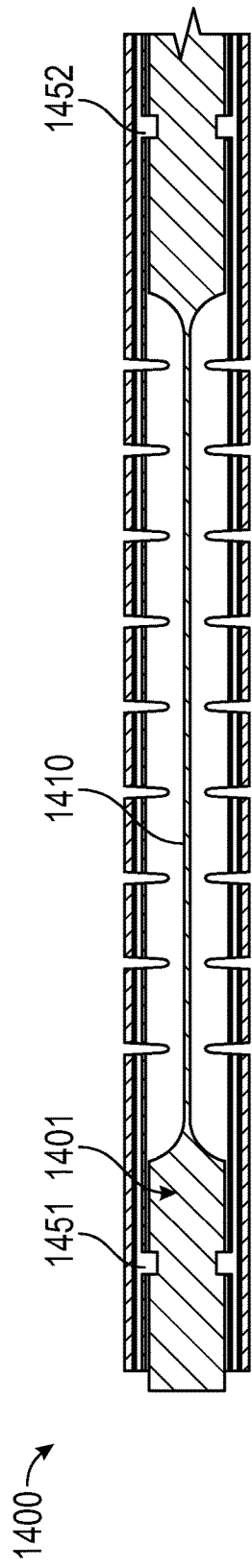
FIG. 14A is a longitudinal, cross-sectional view of a flexible waveguide secured within a lumen of an elongated body by an annular collar protruding inwardly from an inner surface of the elongated body.
Figure 14B:
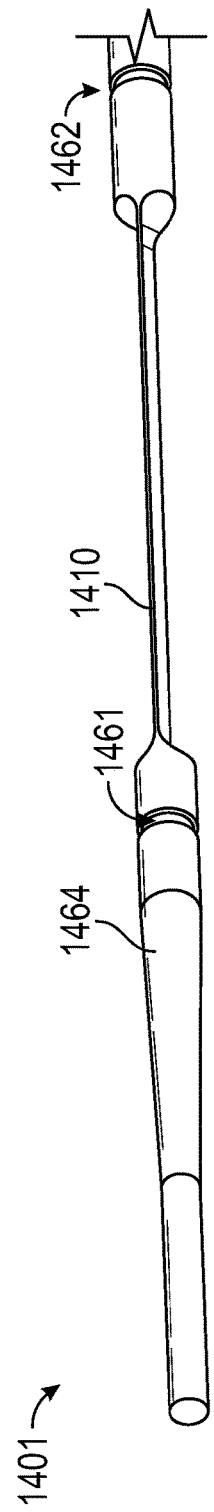
FIG. 14B is a perspective view of the flexible waveguide including a recess configured to receive the annular collar of FIG. 14A.
Figure 14C:
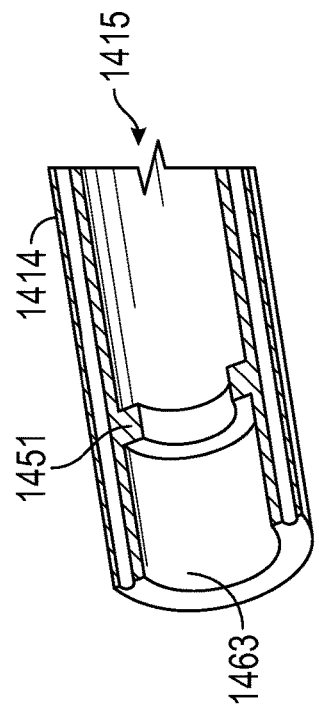
FIG. 14C is a longitudinal, cross-sectional view of the annular collar protruding from the inner surface of the elongated body of FIG. 14A.

Referring particularly to FIGS. 14A to 14C, a support system 1400 for flexible waveguide 1401 is described. The flexible waveguide 1401 includes a first recess 1461 and a second recess 1462 circumferentially formed in an outer surface 1464 of the flexible waveguide 1401. The first and second recesses 1461 and 1462 are shaped and dimensioned to receive annular collars 1451 and 1452, respectively. The annular collars 1451 and 1452 protrude circumferentially from an inner surface 1463 of elongated member 1414 and are configured to be received in the first and second recesses 1461 and 1462, respectively, to secure the flexible waveguide 1401 within lumen 1415 of elongated member 1414. The annular collars 1451, 1452 and recesses 1461, 1462 are positioned proximally and distally, respectively, of articulating portion 1410 to allow articulation of the articulating portion 1410 within lumen 1415 and to prevent contact between articulating portion 1410 and the inner surface 1463 of elongated member 1414.

Referring particularly to FIGS. 15A to 15D, a support system 1500 for flexible waveguide 1501 is described. Removable annular collars 1551 and 1552 are positioned about flexible waveguide 1501. The removable annular collars 1551 and 1552 may each be formed of or include plastic or silicone. The removable annular collars 1551 and 1552 may allow some degree of longitudinal movement within lumen 1515 of elongated member 1514 to prevent stress to the flexible waveguide 1501. The removable annular collars 1551 and 1552 are positioned proximally and distally, respectively, of articulating portion 1510 to allow articulation of the articulating portion 1510 within lumen 1515 and to prevent contact between articulating portion 1510 and the inner surface 1563 of elongated member 1514.

The lumen 1515 may include a first recess 1561 and a second recess 1562 circumferentially formed in the inner surface 1563 of the lumen 1515. The first and second recesses 1561 and 1562 are shaped and dimensioned to receive removable annular collars 1551 and 1552, respectively.

Figure 16:
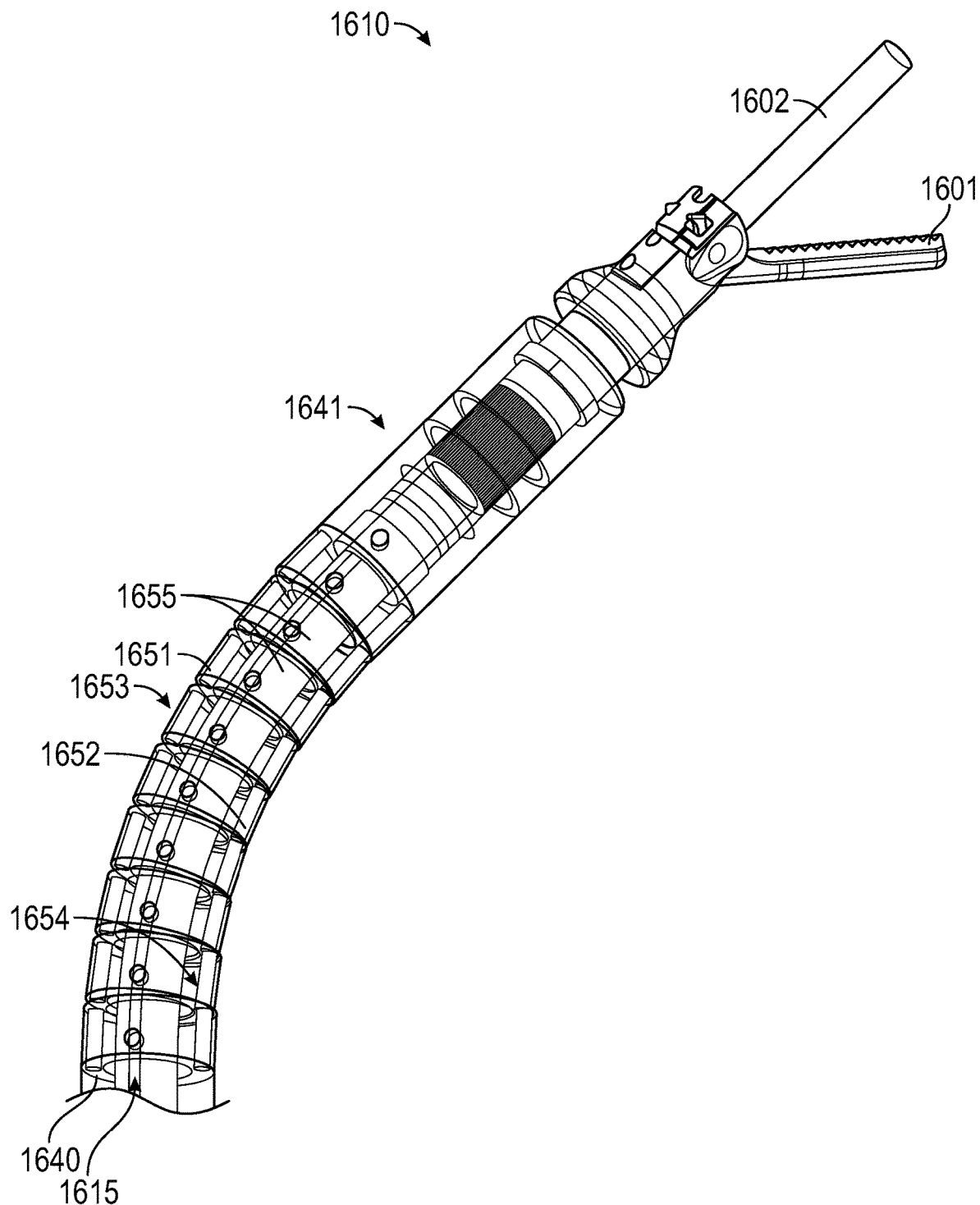
FIG. 16 is a side, perspective view of a cable-drive articulating portion and a rotatable jaw configured for use in accordance with the aspects and features of present disclosure.

Referring particularly to FIG. 16, another surgical instrument 1610 similar to the previously surgical instruments except as contradicted below includes a cable driven articulation system for articulating an outer tube 1641. Outer tube 1641 is disposed about an inner tube 1640. Inner tube 1640 defines a lumen 1615 therethrough.

As an example, a first cable 1651 extending within a first channel 1653 and a second cable 1652 extending within a second channel 1654 may be employed. However, a single cable, or more than two cable may also be employed. Each of the cables 1651 and 1652 may be a tension cable. The cables (e.g., 1651 or 1652) route beside (e.g., on opposing sides of) a waveguide (not illustrated) through respective channels (e.g., 1653 or 1654). The channels may be formed along an inner surface of outer tube 1641, or may be formed along an outer surface of the outer tube 1641. By pulling on one cable, and releasing slack in the other, the articulation pieces (e.g., articulation piece 1655) of the outer tube 1641 engage in their flexed configurations. The articulations pieces 1655 allow a gentle bend to be accomplished by only allowing a certain amount of flex per section. For example, each articulation piece 1655 may allow 5 degrees of flex, and thus using 9 articulation sections allows 45 degrees of total bend. As an example, the articulation pieces 1655 only allows bend in one plane, by use of a pinned joint in each articulation pieces 1655, although multiple bend planes are also contemplated.

Figure 17:
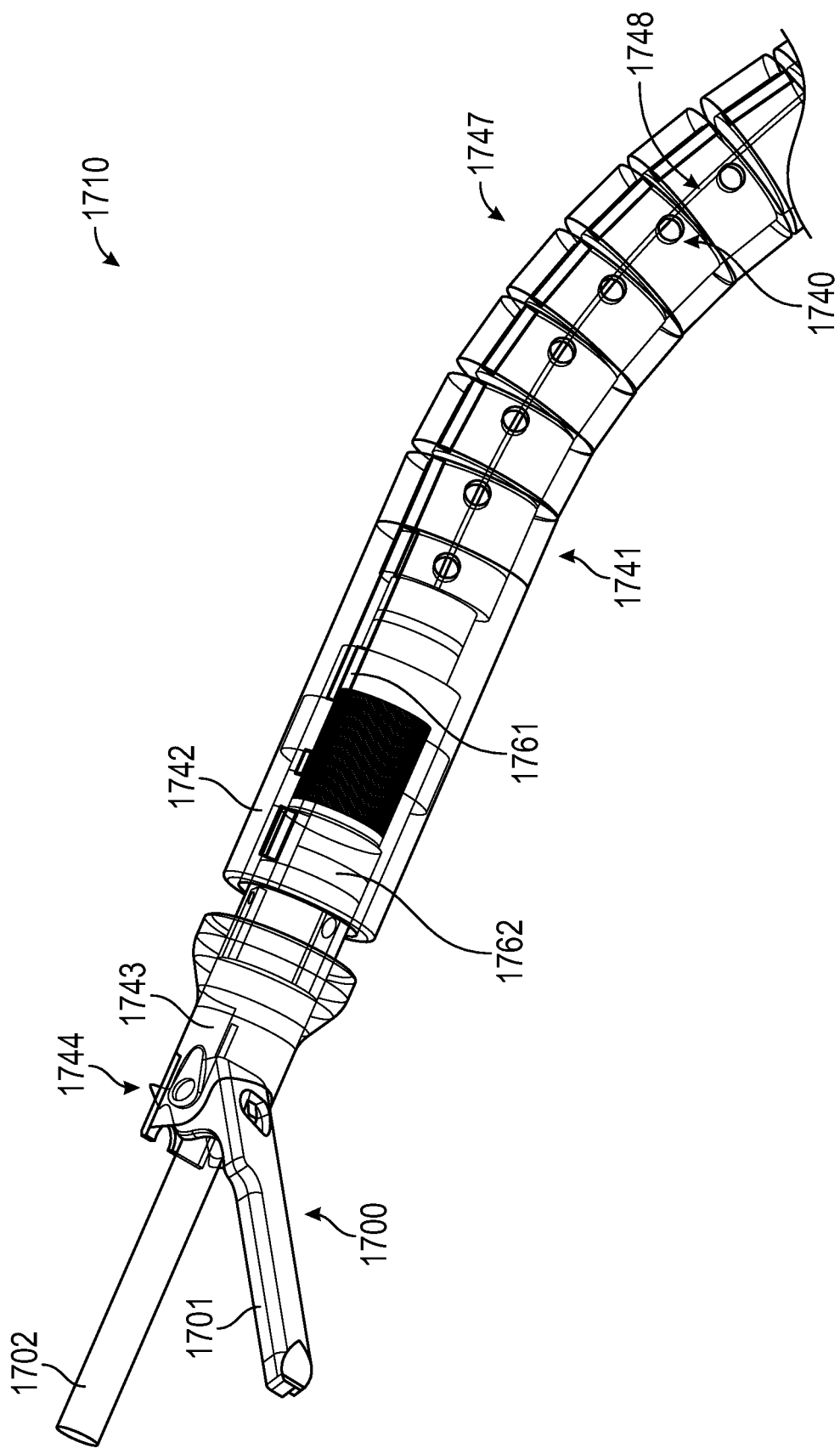
FIG. 17 is another side, perspective view of the articulating portion of FIG. 16 showing a connection between a cable and a yoke configured for actuating the jaw.
Figure 18:
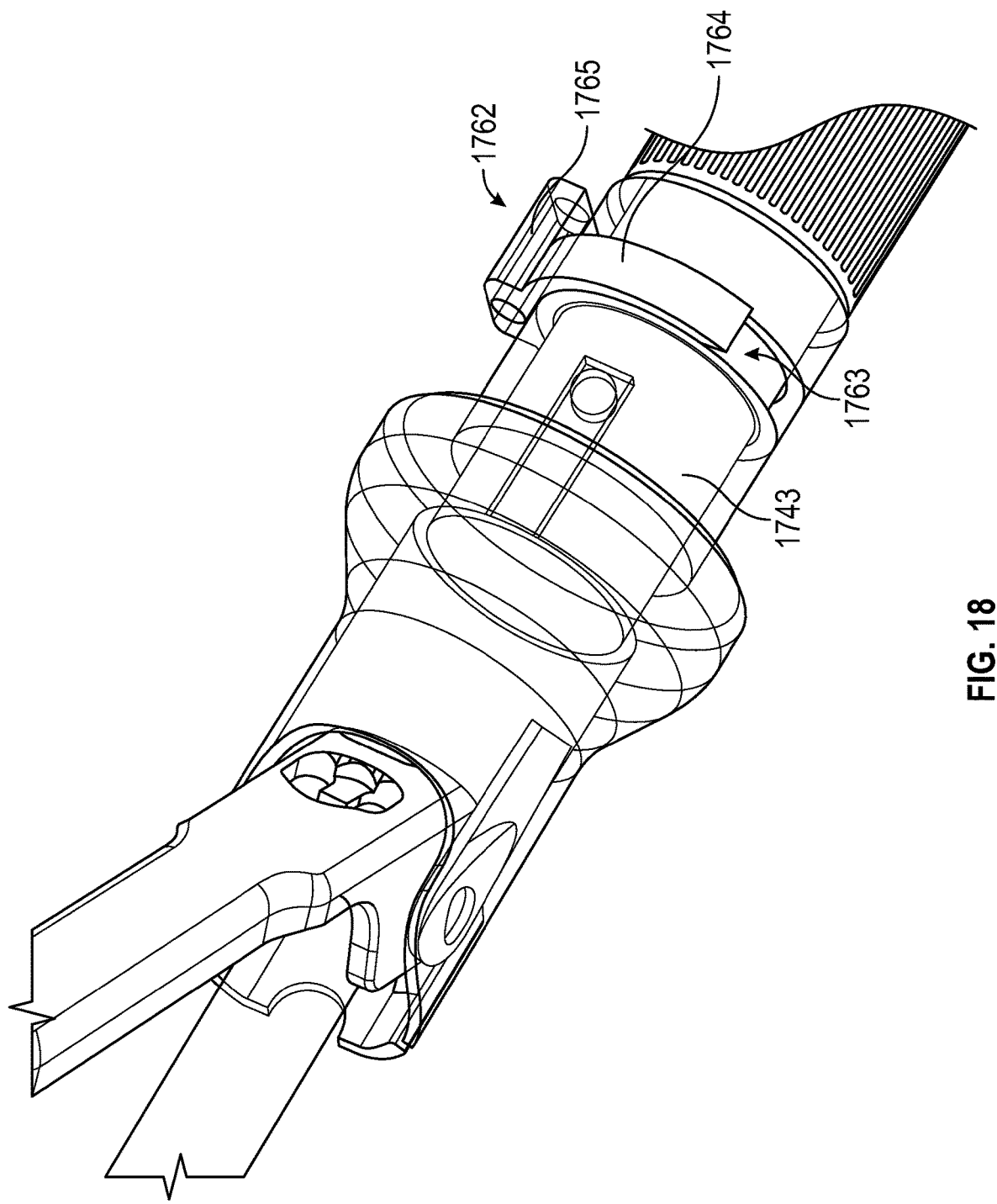
FIG. 18 is an enlarged, side, perspective view of the yoke of FIG. 17 displayed with a proximal portion of an outer tube omitted.
Figure 19:
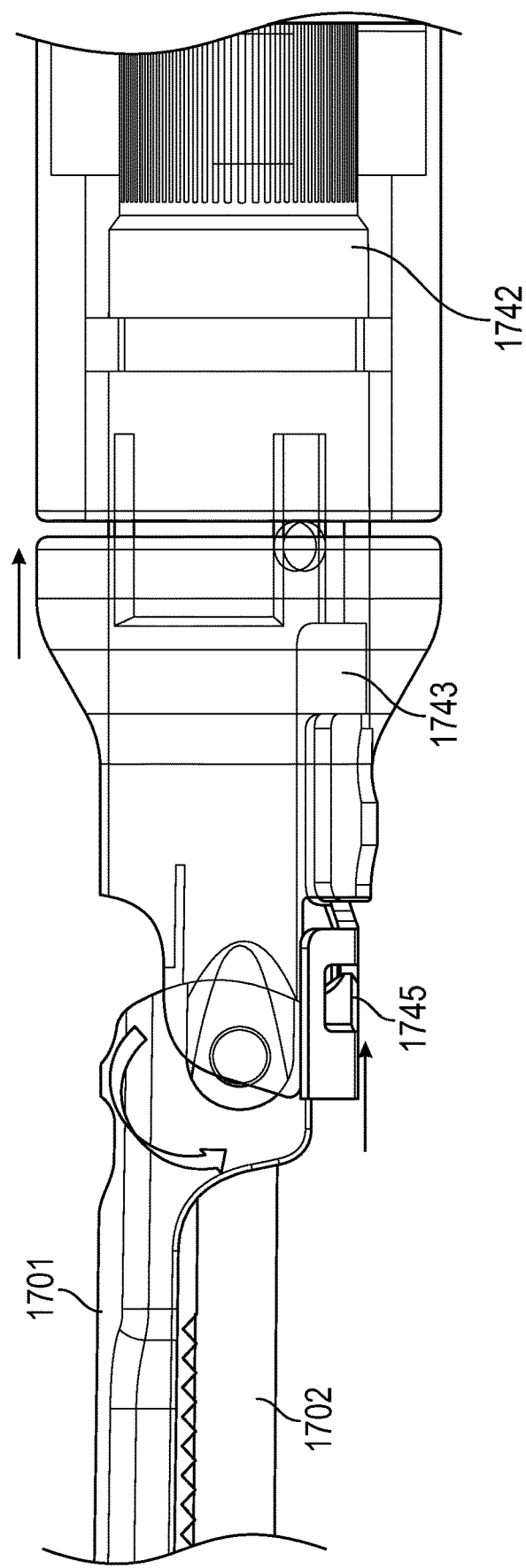
FIG. 19 is a side view illustrating actuation of the jaw of FIG. 17 by sliding a distal portion of the outer tube proximally toward a proximal portion of the outer tube.

Referring particularly to FIGS. 17 to 19, another surgical instrument 1710 similar to the previously surgical instruments except as contradicted below is described including an outer tube 1741. Outer tube 1741 includes a proximal portion 1742 and a distal portion 1743. Outer tube 1741 is positioned about an inner tube 1740. The proximal portion 1742 of the outer tube 1741 defines an articulating section 1747. The articulating section 1747 of the outer tube 1741 at least partially overlaps the articulating section 1748 of the inner tube 1740. The distal portion 1743 of the outer tube 1741 is slidable and rotatable with respect to the proximal portion 1742 of the outer tube 1741. An end effector assembly 1700 is supported at a distal end portion of the inner tube 1740.

The end effector assembly 1700 includes an ultrasonic blade 1702 and a jaw 1701 configured to rotate about the ultrasonic blade 1702. The jaw 1701 is configured to move between an open position (see, e.g., FIG. 17) and a clamping position (see, e.g., FIG. 19) with respect to the ultrasonic blade 1702 and to rotate radially about the ultrasonic blade 1702 to enable the capture and treatment of tissue therebetween in plural rotational orientations of the jaw 1701 relative to the ultrasonic blade 1702.

The jaw 1701 is actuated with respect to ultrasonic blade 1702 by proximally sliding the distal portion 1743 of the outer tube 1741 toward the proximal portion 1742 of the outer tube 1741 (see, e.g., FIG. 19) and relative to the jaw assembly 1744 which is supported by the inner tube 1740. The distal portion 1743 of the outer tube 1741 engages feet (e.g., 1745) of the jaw assembly 1744 to actuate the jaw 1701 with respect to the ultrasonic blade 1702.

In order to urge the distal portion 1743 of the outer tube 1741 to slide back and forth, cable tension via cable 1761 is used to pull the distal portion 1743 of the outer tube 1741 proximally and a spring (not shown) is used to bias and return the distal portion 1743 of the outer tube 1741 to its original position in the absence of tension on the cable 1761. The cable 1761 may be a tension cable.

In order to allow rotation of the jaw 1701 without rotating the cable 1761, a yoke 1762 coupled with cable 1761 is utilized. The yoke 1762 sits in a groove 1763 on the distal portion 1743 of the outer tube 1741 allowing rotation of the distal portion 1743 of the outer tube 1741, but when tension is applied to pull the cable 1761, the yoke 1762 is pulled and the distal portion 1743 of the outer tube 1741 is moved proximally along with the yoke 1762.

The yoke 1762 includes a first curved arm 1764 and a second curved arm (not shown, but substantially a mirror image of the first curved arm 1764). The curved arms (e.g., arm 1764) rotatably slide along groove 1763 formed in the distal portion 1743 of the outer tube 1741. The yoke 1762 includes a guide block 1765 extending along a longitudinal axis of the proximal portion 1742 of the outer tube 1741. The guide block 1765 slides along the proximal portion 1742 of the outer tube 1741 as the distal portion 1743 of the outer tube 1741 is moved proximally along with the yoke 1762.

Figure 20:
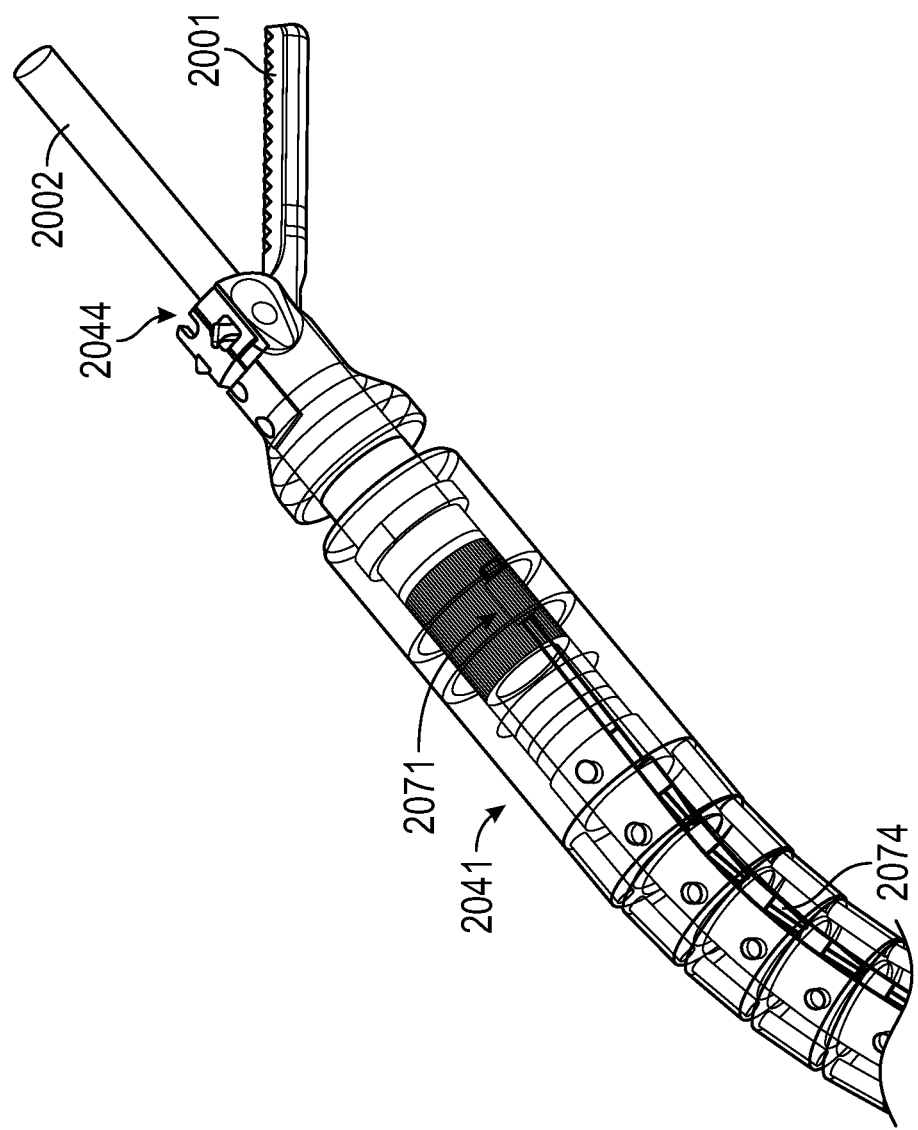
FIG. 20 is still another side, perspective view of a cable configured for rotating a geared mechanism to rotate the jaw of FIG. 17.
Figure 21:
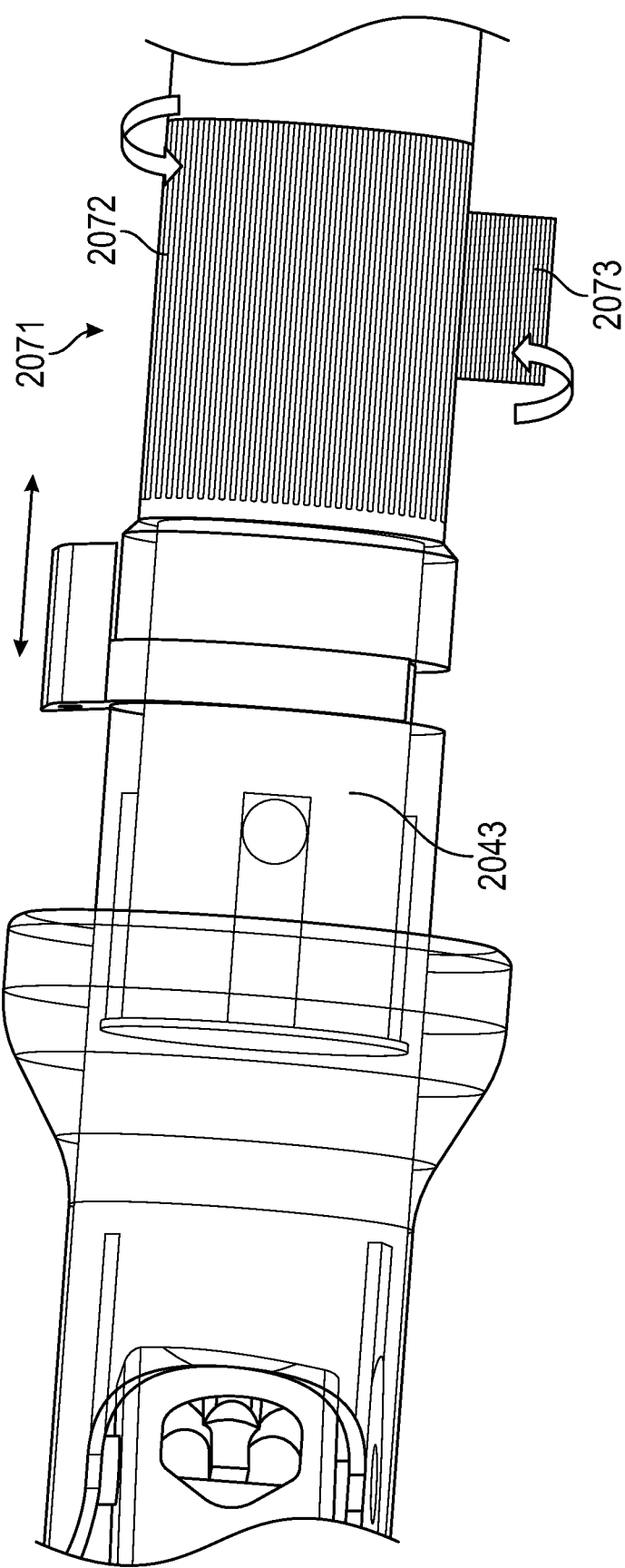
FIG. 21 is an enlarged, side view of the geared mechanism of FIG. 20.

Referring particularly to FIGS. 20 to 21, jaw assembly 2044 including a jaw 2001 is rotated by a geared mechanism 2071 including a drive gear 2072 operably coupled to the jaw assembly 2044 and an input gear 2073 engaged with the drive gear 2072 such that rotation of the input gear 2073 rotates the drive gear 2072 to rotate the jaw assembly 2044 and jaw 2001.

As an example, a torque cable 2074, which is coupled to a robotic drive motor (not shown), extends along the length of the surgical instrument to actuate input gear 2073. The geared mechanism 2071 may be positioned in the distal portion 2043 of the outer tube (see, e.g., outer tube 2041).

Figure 22:
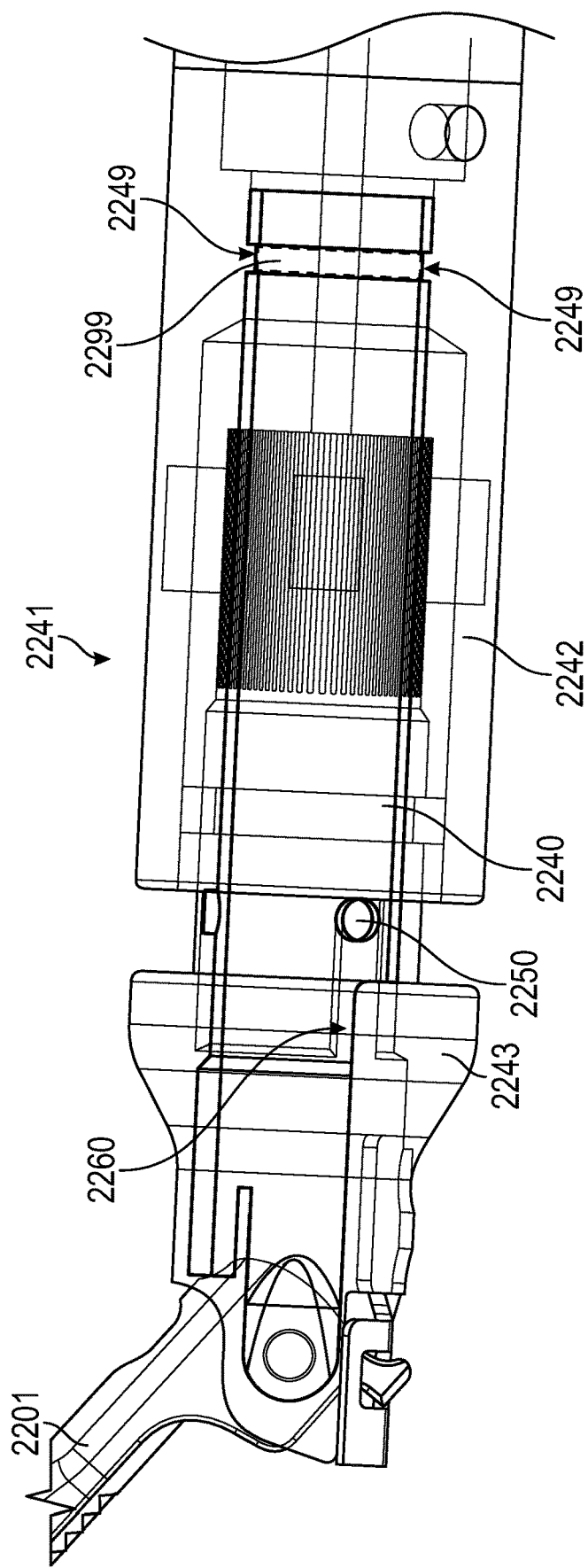
FIG. 22 is an enlarged, side view illustrating the inner tube in phantom in which the inner tube is rotatably coupled to the proximal portion of the outer tube.

Referring particularly to FIG. 22, the inner tube 2240 is rotatably coupled to the proximal portion 2242 of the outer tube 2241. The inner tube 2240 does not slide proximal/distal with the distal portion 2243 outer tube 2241, but both the inner tube 2240 and the distal portion 2243 of the outer tube 2241 rotate with one another. The inner tube 2240 may include grooves 2249 and a retaining ring 2299 for rotatably coupling the inner tube 2240 to the proximal portion 2242 of the outer tube 2241.

The inner tube 2240 may include bosses 2250 that reside in slots 2260 of the distal portion 2243 of the outer tube 2241. The slots 2260 engage the bosses 2250 to drive rotation of the inner tube 2240 along with rotation of the distal portion 2243 of the outer tube 2241. The bosses 2250 and slots 2260 allow the distal portion 2243 of the outer tube 2241 to slide proximal/distal in relation to the inner tube 2240 to actuate the jaw 2201.

Referring particularly to FIGS. 23 to 26, a surgical instrument 2610 includes an outer tube 2381 configured to rotate about an inner tube 2482. A jaw 2601 is pivotably supported by the outer tube 2381. Rotation of the outer tube 2381 about the inner tube 2482 correspondingly rotates the jaw 2601 about the ultrasonic blade 2602 extending from the inner tube 2482. The inner tube 2482 and the outer tube 2381 may each be semi-rigid shafts (e.g., including both rigid and flexible portions). The outer tube 2381 drives rotation of the jaw 2601.

As an example, the outer tube 2381 may be welded directly to jaw assembly 2644 that includes jaw member 2601. Thus, rotation of the jaw 2601 is driven by rotation of the entire outer tube 2381 (see, e.g., FIG. 26).

Figure 23:
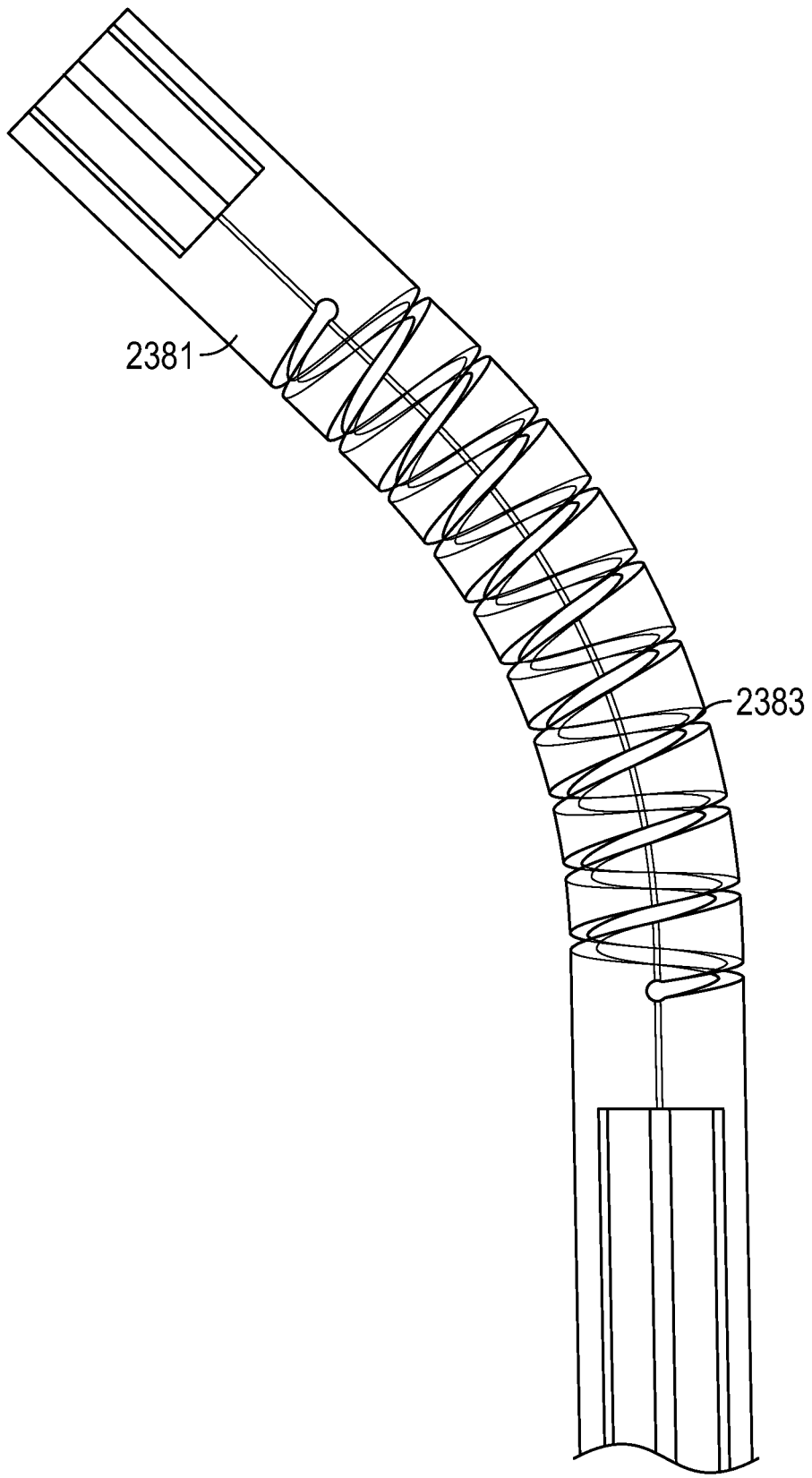
FIG. 23 is a side view of an articulating portion of an outer tube configured for use in accordance with the aspects and features of present disclosure.
Figure 24:
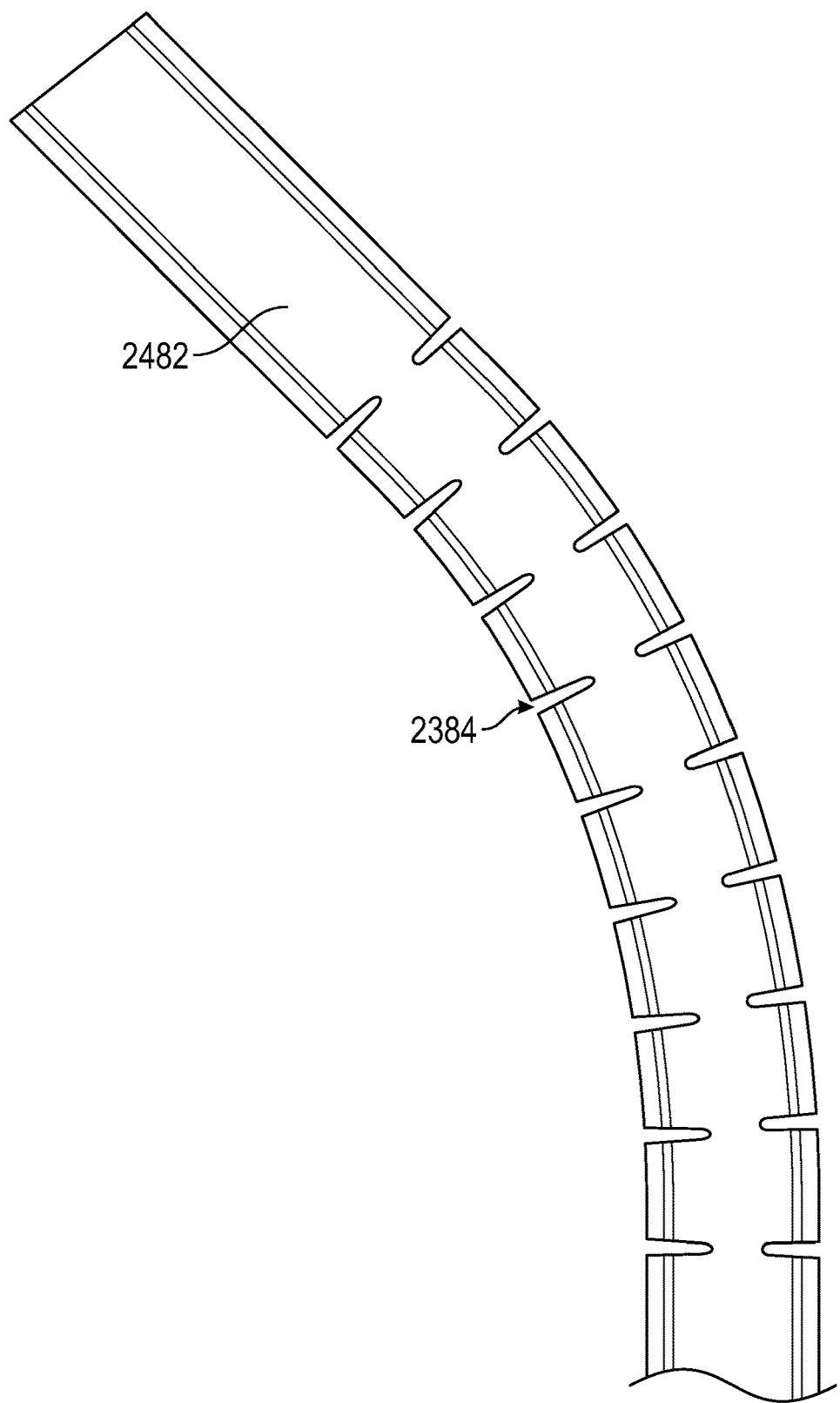
FIG. 24 is a side view of an articulating portion of an inner tube configured for use in accordance with the aspects and features of present disclosure.

The outer tube 2381 is configured to articulate in any direction (see, e.g., FIG. 23). The inner tube 2482 is configured to articulate substantially along a single plane (see, e.g., FIG. 24), although multiple plates of articulation are also contemplated. The outer tube 2381 includes a spiral cutout 2383 configured to allow articulation in any direction and to impart rotation that is carried to a jaw assembly (e.g., jaw assembly 2644). The configuration of the spiral cutout 2383 may be modified to increase or decrease an amount of torque applied to a jaw assembly (e.g., jaw assembly 2644). The inner tube 2482 includes a plurality of pairs of opposed cutouts 2384 spaced apart from each other. The plurality of pairs of cutouts 2384 allow articulation of the inner tube 2482 substantially along a single plane (in directions substantially perpendicular to the cut-outs 2384). The size and spacing of the cutouts 2384 permits a predetermined degree of flex along the single plane.

A flexible waveguide, as described herein, may be rotatably fixed within the inner tube 2482. The flexible waveguide is coupled to ultrasonic blade 2502.

Figure 25:
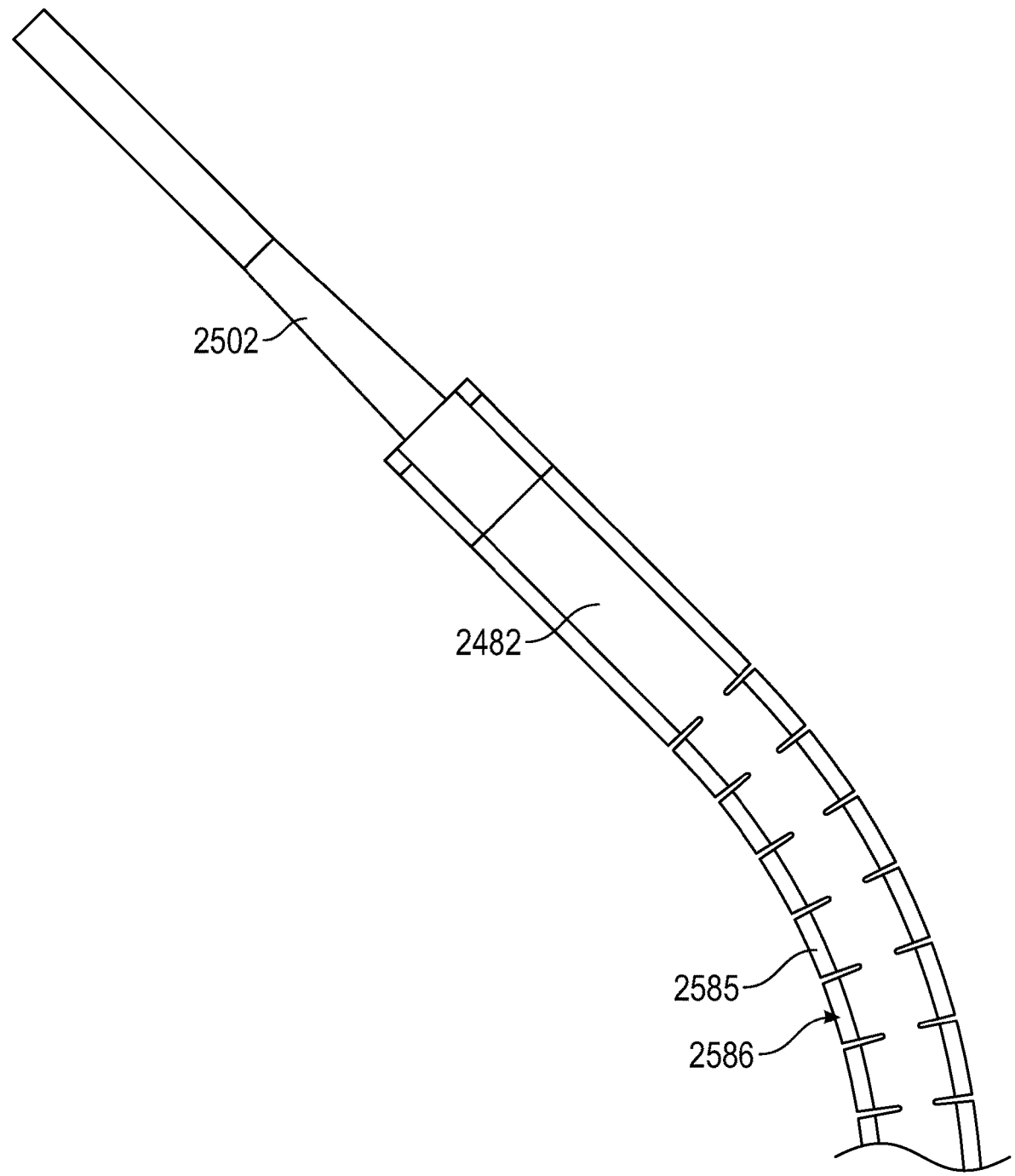
FIG. 25 illustrates cable channels formed in the inner tube of FIG. 24 configured to receive cables for articulating the articulating portion of the inner tube.
Figure 26:
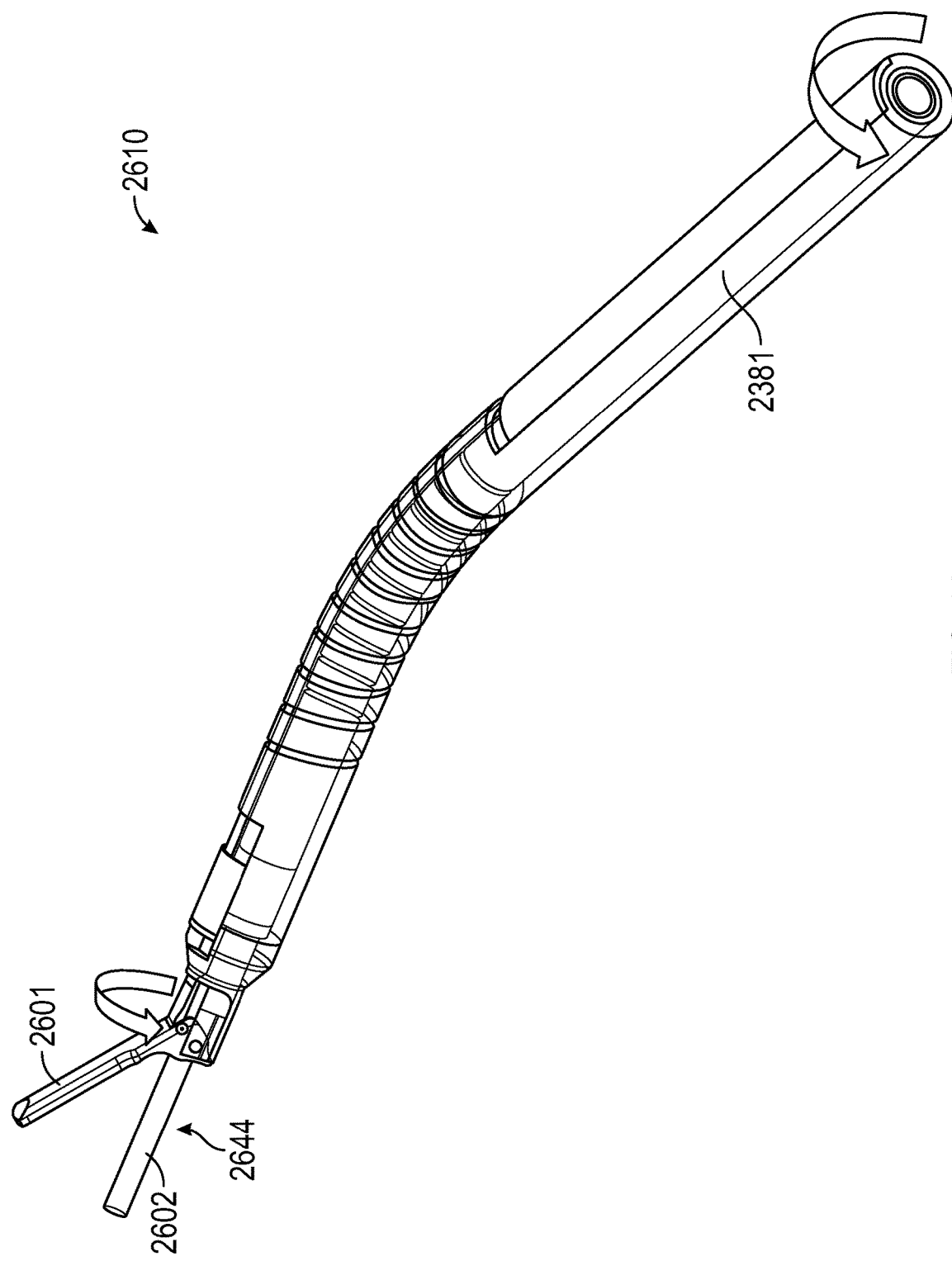
FIG. 26 illustrates the outer tube of FIG. 23 coupled to a jaw assembly and configured to rotate about the inner tube of FIG. 24 to rotate the jaw assembly.

Referring particularly to FIGS. 25 and 26, articulation of the surgical instrument 2610 may be cable driven. Similarly to the cable system described with reference to FIG. 16, cables 2585 may extend within channels 2586 formed along the inner tube 2482.

A barrier layer (not illustrated), such as Teflon sleeve, may be positioned between the outer tube 2381 and the inner tube 2482.

Figure 27:
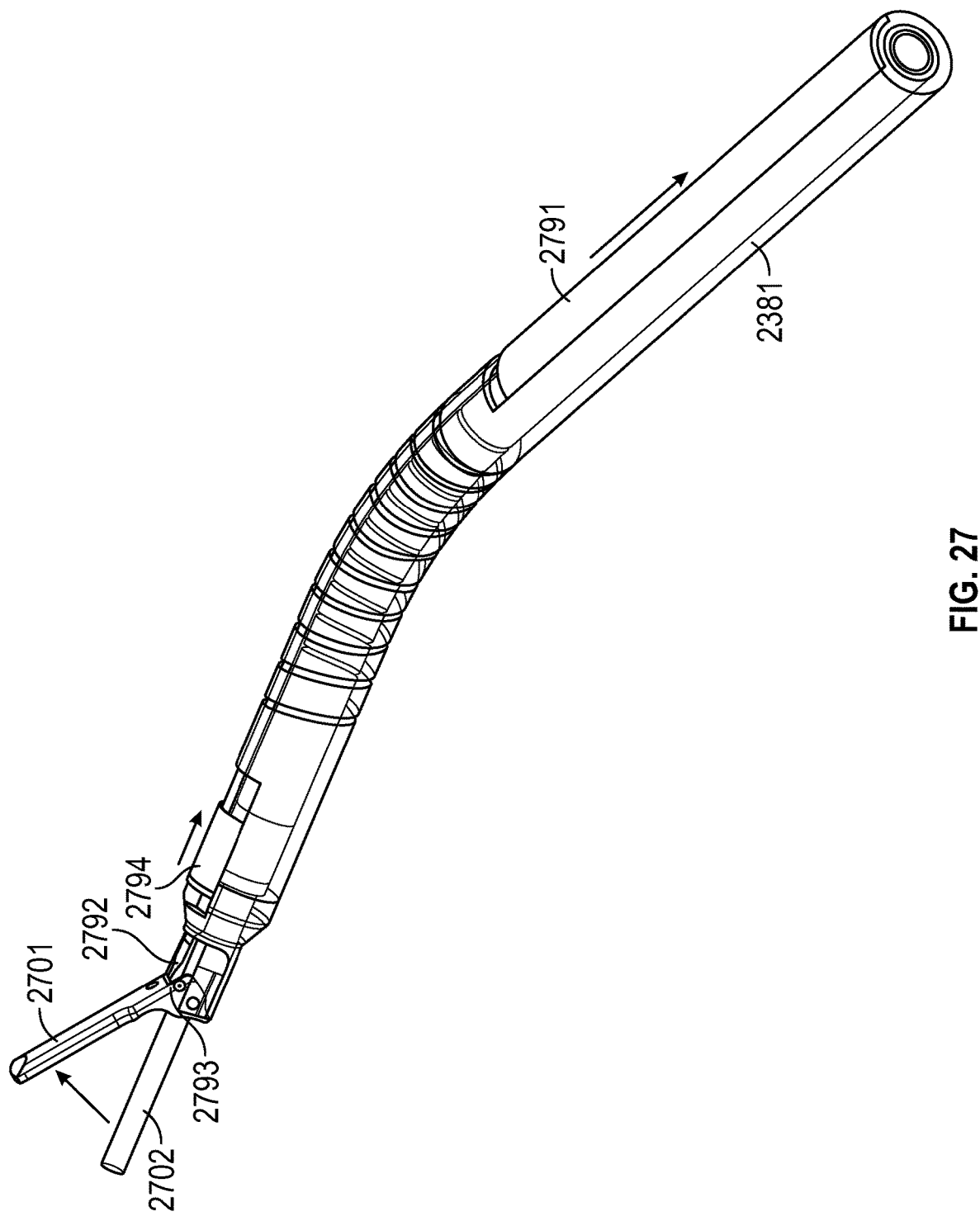
FIG. 27 illustrates opening of the jaw of FIG. 26 by a link system coupled to the jaw.
Figure 28:
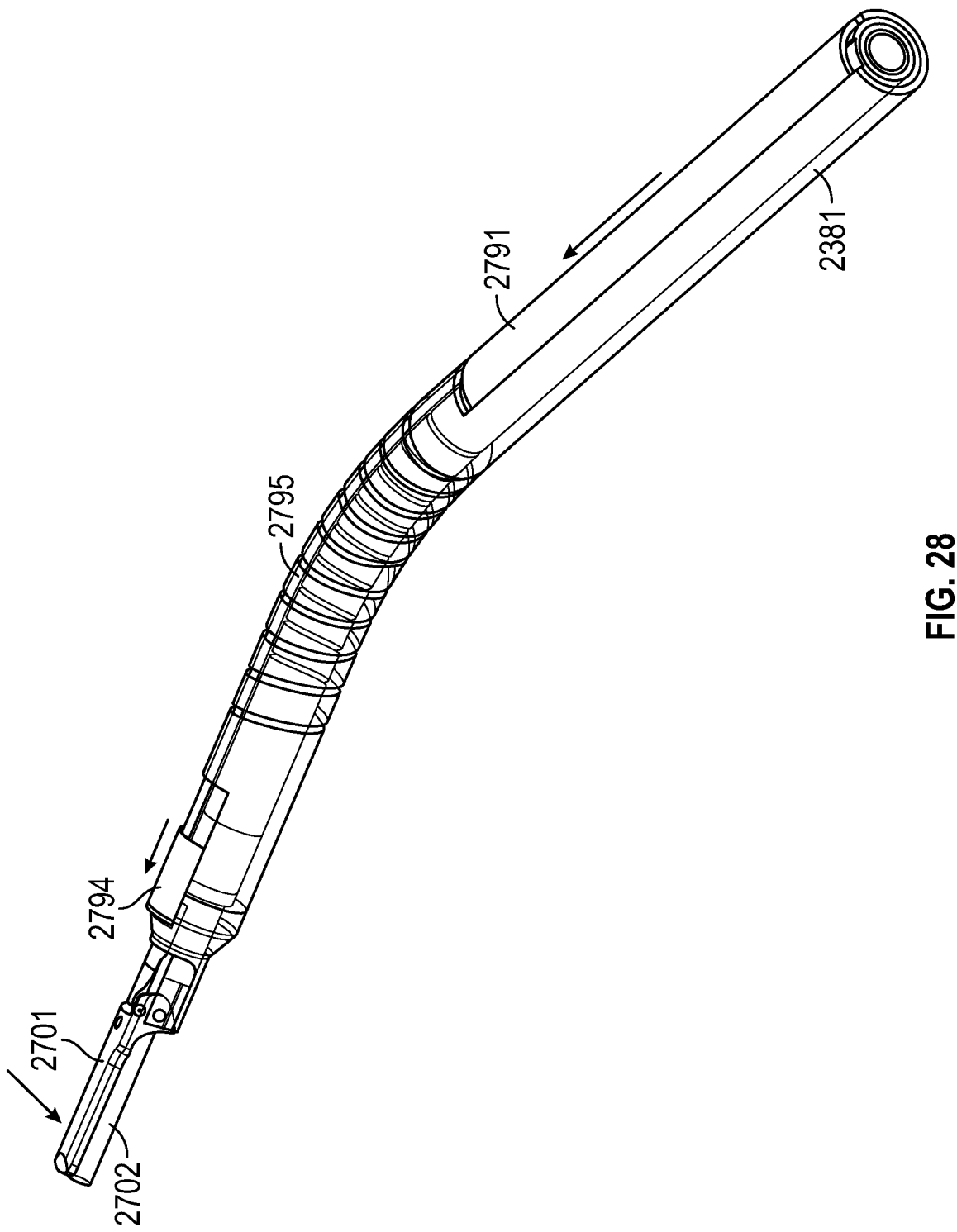
FIG. 28 illustrates actuation of the jaw of FIG. 27 by the link system.

Referring to FIGS. 27 to 28, actuation of the jaw 2701 relative to the ultrasonic blade 2702 is described.

A direct drive including links 2791 and 2794 extending along the outer tube 2381 is operably connected with the jaw 2701. A distal link 2792 is connected to a pin 2793 that drives the opening and closing of the jaw 2701. As an example, pulling on the links 2791 and 2794 drives the jaw 2701 open (see, e.g., FIG. 27), and pushing on the links 2791 and 2794 drives the jaw 2701 to a clamped position (see, e.g., FIG. 28); however, this arrangement may be reversed such that pulling on the links 2791 and 2794 drives the jaw 2701 closed. As an example, a superelastic nitinol wire 2795 (see, e.g., FIG. 28) may extend along the articulating portion of outer tube 2381 to connect the links 2791 and 2794 to each other.

From the foregoing and with reference to the various figure drawings, those skilled in the art will appreciate that certain modifications can also be made to the disclosure without departing from the scope of the same. While several embodiments of the disclosure have been shown in the drawings, it is not intended that the disclosure be limited thereto, as it is intended that the disclosure be as broad in scope as the art will allow and that the specification be read likewise. Therefore, the above description should not be construed as limiting, but merely as exemplifications of particular embodiments. Those skilled in the art will envision other modifications within the scope and spirit of the claims appended hereto.

What is claimed is:

1. An elongated body of a surgical instrument, comprising:
   an inner tube including an articulating section and defining a lumen therethrough;
   an outer tube disposed about the inner tube and including a proximal portion and a distal portion, the proximal portion of the outer tube defining an articulating section, wherein the articulating section of the outer tube at least partially overlaps the articulating section of the inner tube, the distal portion of the outer tube slidable with respect to the proximal portion of the outer tube;
   an end effector assembly disposed at a distal end portion of the inner tube, the end effector assembly including an ultrasonic blade defining a longitudinal axis and a jaw configured to rotate about the longitudinal axis to plural rotational orientations of the jaw relative to the ultrasonic blade, the jaw configured to move between an open position and a clamping position with respect to the ultrasonic blade to capture and treat tissue therebetween in each of the plural rotational orientations of the jaw relative to the ultrasonic blade; and
   a flexible waveguide extending through the lumen of the inner tube, a distal end portion of the flexible waveguide connected with the ultrasonic blade of the end effector assembly,
   wherein sliding the distal portion of the outer tube with respect to the proximal portion of the outer tube actuates the jaw with respect to the ultrasonic blade between the open position and the clamping position.

2. The surgical instrument of claim 1, further including:
   a cable extending along the proximal portion of the outer tube, the cable operably coupled to the distal portion of the outer tube, the cable configured to slide the distal portion of the outer tube in a proximal direction toward the proximal portion of the outer tube to actuate the jaw with respect to the ultrasonic blade to the clamping position; and
   a spring operably coupled to the distal portion of the outer tube, the spring configured to bias the distal portion of the outer tube in a distal direction away from the proximal portion of the outer tube, the spring configured to bias the jaw with respect to the ultrasonic blade to the open position or a closed position.

3. The surgical instrument of claim 2, further including a yoke operably coupled to the cable and the distal portion of the outer tube, wherein pulling the cable in the proximal direction pulls the distal portion of the outer tube in the proximal direction to actuate the jaw, the yoke configured to allow the distal portion of the outer tube to rotate with respect to the proximal portion of the outer tube.

4. The surgical instrument of claim 3, wherein the yoke includes a first curved arm and a second curved arm, the first and second curved arms configured to rotatably slide along a groove formed in the distal portion of the outer tube, the yoke further including a guide block extending along a longitudinal axis of the proximal portion of the outer tube, the guide block configured to slide along the proximal portion of the outer tube.

5. The surgical instrument of claim 1, further including:
   a drive gear operably coupled to the jaw assembly; and
   an input gear engaged with the drive gear, wherein rotation of the input gear rotates the drive gear to rotate the jaw assembly.

6. The surgical instrument of claim 5, further including a torque cable operably coupled to the input gear, wherein rotation of the torque cable rotates the input gear.

7. The surgical instrument of claim 1, wherein the inner tube is rotatably coupled to the proximal portion of the outer tube.

8. The surgical instrument of claim 7, wherein the inner tube includes a groove and the proximal portion of the outer tube includes a retaining ring positioned in the groove to rotatably couple the inner tube to the proximal portion of the outer tube.

9. The surgical instrument of claim 7, wherein the distal portion of the outer tube includes at least one slot, and the inner tube includes at least one boss slidably positioned in the at least one slot, wherein the at least one slot allows the distal portion of the outer tube to move proximally and distally with respect to the inner tube, and wherein the inner tube rotates in unison with the outer tube.

10. A surgical instrument, comprising:
    a housing having an elongated body extending distally therefrom, the elongated body including:
    an inner tube including an articulating section and defining a lumen therethrough;
    an outer tube disposed about the inner tube and including a proximal portion and a distal portion, the proximal portion of the outer tube defining an articulating section, wherein the articulating section of the outer tube at least partially overlaps the articulating section of the inner tube, the distal portion of the outer tube slidable with respect to the proximal portion of the outer tube;
    an end effector assembly supported at a distal end portion of the inner tube, the end effector assembly including an ultrasonic blade defining a longitudinal axis and a jaw configured to rotate about the longitudinal axis to plural rotational orientations of the jaw relative to the ultrasonic blade, the jaw configured to move between an open position and a clamping position with respect to the ultrasonic blade to capture and treat tissue therebetween in each of the plural rotational orientations of the jaw relative to the ultrasonic blade; and
    a flexible waveguide extending through the lumen of the inner tube, a distal end portion of the flexible waveguide connected with the ultrasonic blade of the end effector assembly,
    wherein sliding the distal portion of the outer tube with respect to the proximal portion of the outer tube actuates the jaw with respect to the ultrasonic blade between the open position and the clamping position.

11. The surgical instrument of claim 10, further including:
    a cable extending along the proximal portion of the outer tube, the cable operably coupled to the distal portion of the outer tube, the cable configured to slide the distal portion of the outer tube in a proximal direction toward the proximal portion of the outer tube to actuate the jaw with respect to the ultrasonic blade to the clamping position; and
    a spring operably coupled to the distal portion of the outer tube, the spring configured to bias the distal portion of the outer tube in a distal direction away from the proximal portion of the outer tube, the spring configured to bias the jaw with respect to the ultrasonic blade to the open position or a closed position.

12. The surgical instrument of claim 11, further including a yoke operably coupled to the cable and the distal portion of the outer tube, wherein pulling the cable in the proximal direction pulls the distal portion of the outer tube in the proximal direction to actuate the jaw, the yoke configured to allow the distal portion of the outer tube to rotate with respect to the proximal portion of the outer tube.

13. The surgical instrument of claim 12, wherein the yoke includes a first curved arm and a second curved arm, the first and second curved arms configured to rotatably slide along a groove formed in the distal portion of the outer tube, the yoke further including a guide block extending along a longitudinal axis of the proximal portion of the outer tube, the guide block configured to slide along the proximal portion of the outer tube.

14. The surgical instrument of claim 10, wherein the inner tube is rotatably coupled to the proximal portion of the outer tube.

15. The surgical instrument of claim 14, wherein the inner tube includes a groove and the proximal portion of the outer tube includes a retaining ring positioned in the groove to rotatably couple the inner tube to the proximal portion of the outer tube.

16. The surgical instrument of claim 14, wherein the distal portion of the outer tube includes at least one slot, and the inner tube includes at least one boss slidably positioned in the at least one slot, wherein the at least one slot allows the distal portion of the outer tube to move proximally and distally with respect to the inner tube, and wherein the inner tube rotates in unison with the outer tube.

* * * * *